United States Patent
Langer et al.

(10) Patent No.: US 12,364,759 B2
(45) Date of Patent: Jul. 22, 2025

(54) POLYMER-PARTICLE LIGHT-CLEAVABLE CARRIER SYSTEMS FOR PHOTODYNAMIC THERAPY

(71) Applicants: WESTFÄLISCHE WILHELMS-UNIVERSITÄT MÜNSTER, Münster (DE); UNIVERSITÄT PADERBORN, Paderborn (DE); BIOLITEC RESEARCH GMBH, Jena (DE)

(72) Inventors: Klaus Langer, Münster (DE); Juliane Anderski, Bernkastel-kues (DE); Laura Mahlert, Bochum (DE); Dennis Mulac, Münster (DE); Dirk Kuckling, Paderborn (DE); Jingjiang Sun, Paderborn (DE); Wolfgang Birnbaum, Paderborn (DE); Arno Wiehe, Berlin (DE); Gerhard Dieter Wieland, Jena (DE); Volker Albrecht, Nuthetal (DE)

(73) Assignees: WESTFÄLISCHE WILHELMS-UNIVERSITÄT MÜNSTER, Münster (DE); UNIVERSITÄT PADERBORN, Paderborn (DE); BIOLITEC RESEARCH GMBH, Jena (DE)

( * ) Notice: Subject to any disclaimer, the term of this patent is extended or adjusted under 35 U.S.C. 154(b) by 992 days.

(21) Appl. No.: 17/278,880

(22) PCT Filed: Sep. 24, 2019

(86) PCT No.: PCT/EP2019/075653
§ 371 (c)(1),
(2) Date: Mar. 23, 2021

(87) PCT Pub. No.: WO2020/064701
PCT Pub. Date: Apr. 2, 2020

(65) Prior Publication Data
US 2022/0047705 A1  Feb. 17, 2022

(30) Foreign Application Priority Data
Sep. 24, 2018 (EP) .................... 18196319

(51) Int. Cl.
| | | |
|---|---|---|
| A61K 41/00 | (2020.01) | |
| A61K 31/409 | (2006.01) | |
| A61K 47/34 | (2017.01) | |
| C07D 319/06 | (2006.01) | |
| C08G 64/02 | (2006.01) | |
| C08G 64/18 | (2006.01) | |
| C08G 64/30 | (2006.01) | |

(52) U.S. Cl.
CPC ........ *A61K 41/0057* (2013.01); *A61K 31/409* (2013.01); *A61K 41/0042* (2013.01); *A61K 47/34* (2013.01); *C07D 319/06* (2013.01); *C08G 64/0241* (2013.01); *C08G 64/183* (2013.01); *C08G 64/30* (2013.01); *C08G 64/305* (2013.01)

(58) Field of Classification Search
None
See application file for complete search history.

(56) References Cited

U.S. PATENT DOCUMENTS 9,388,276 B2 * 7/2016 Song .................. A61L 27/18
10,160,829 B2 * 12/2018 Yang ................... C08G 63/54

FOREIGN PATENT DOCUMENTS

WO  WO 2011/071970 A2   6/2011
WO  WO 2013/169953 A1  11/2013

OTHER PUBLICATIONS

IUPAC. What are Polymers? Retrieved from the internet on Feb. 15, 2024, https://iupac.org/polymer-edu/what-are-polymers/. (Year: 2024).*
International Preliminary Report on Patentability and Written Opinion mailed Apr. 1, 2021 from corresponding International Application No. PCT/EP2019/075653.
Juliane Anderski et al. "Light-responsive nanoparticles based on new polycarbonate polymers as innovative drug delivery systems for photosensitizers in PDT" International Journal of Pharmaceutics; vol. 557, Dec. 22, 2018; pp. 182-191.
Jingjiang Sun "Use of Light-Degradable Aliphatic Polycarbonate Nanoparticles as Drug Carrier for Photosensitizer" Biomacromolecules; vol. 19, No. 12; Nov. 15, 2018; pp. 4677-4690.
Jingjiang Sun "Preparation of Light-Responsive Aliphatic Polycarbonate via Versatile Polycondensation for Controlled Degradation" Macromolecular Chemistry and Physics; vol. 22, No. 5, Mar. 1, 2019; p. 1800539 (pp. 1 of 5).
International Search Report mailed Dec. 18, 2019 from corresponding International Application No. PCT/EP2019/075653.

* cited by examiner

*Primary Examiner* — James H Alstrum-Acevedo
*Assistant Examiner* — Lauren Wells
(74) *Attorney, Agent, or Firm* — Davidson Kappel LLC

(57) ABSTRACT

The present invention generally relates to the formation, chemistry and application of biologically active compositions. More particularly, the present invention relates to certain dyes, specifically porphyrin and chlorin derivatives, in combination with inventive polymers, i.e. light-cleavable polymers, that can be used as photosensitizer compositions for a wide range of light irradiation treatments such as photodynamic therapy of cancer, infections and other diseases. The dye derivatives may either be adsorbed on, or incorporated in, or attached to specific polymers, which as well form part of the invention.

16 Claims, 13 Drawing Sheets

POLYMER-PARTICLE LIGHT-CLEAVABLE CARRIER SYSTEMS FOR PHOTODYNAMIC THERAPY

This application is a U.S. national phase application under 35 U.S.C of 371 of International Application No. PCT/EP2019/075653, filed Sep. 24, 2019, which claims priority of European Patent Application No. EP 18196319.0, filed Sep. 24, 2018, the disclosures of which are hereby incorporated by reference herein.

The present invention generally relates to the formation, chemistry and application of biologically active compositions. More particularly, the present invention relates to certain dyes, specifically porphyrin and chlorin derivatives, in combination with inventive polymers that can be used as photosensitizer compositions for a wide range of light irradiation treatments such as photodynamic therapy of cancer, infections and other diseases. The dye derivatives may either be adsorbed on, or incorporated in, or attached to specific polymers, which as well form part of the invention.

Cancer is one of the main causes of death worldwide. Though many therapeutic approaches are known there is still need for new active substances and therapies that can be applied to tumors which cannot successfully be treated by conventional chemotherapeutics. One of those newer therapeutic approaches is photodynamic therapy (PDT).

PDT is now being explored for use in a variety of medical applications, and particularly is a well-recognized treatment for the destruction of tumors. Photodynamic therapy uses light and a photosensitizer, also called a dye in the sense of the present invention, to achieve its desired medical effect. A large number of naturally occurring and synthetic dyes have been evaluated as potential photosensitizers for PDT. Perhaps the most widely studied class of photosensitizers are tetrapyrrolic macrocyclic compounds. Among them, especially porphyrins and chlorins have been tested for their PDT efficacy.

The photodynamic effect is only observed where the three necessary components, the photosensitizer, light and oxygen (which is present in the cells) are present at the same time. Anti-tumor photosensitizers are usually highly lipophilic or amphiphilic compounds as these preferably accumulate in membranes where the generated reactive oxygen species (ROS, most prominently singlet oxygen) can do most harm to the (tumor) cells. This high lipophilicity of anti tumor photosensitizers poses difficulties for their formulation.

Photosensitizers for anti-tumor PDT are highly lipophilic compounds with a low or no water solubility. So, for the administration of photosensitizers suitable pharmaceutical formulations are needed.

Nanoparticle formulations of photosensitizers for tumor treatment can benefit from the EPR effect (enhanced permeability and retention effect) of malign tissue where particles of a certain size can more easily leave the blood stream due to the specific structure of tumor tissue and where they are retained for longer periods due to the underdeveloped lymphatic system. In the art, a number of methods are described to connect photosensitizer molecules to macromolecular or nanoparticle carriers.

Example for possible carrier systems comprise polymers. International Publications N° WO2008130181A1 by Kwon et al. and International Publication N° WO2011071970 by Langer et al. disclose polymers as carrier systems for pharmaceuticals. However, specifically for photosensitizers there is a need to release the photosensitizer molecule from the nanoparticle or the macromolecular carrier, given that the close proximity of the photosensitizer molecules to the carrier system changes their photophysical behavior and may lead to a suppression of the desired action, i.e. the generation of reactive oxygen species (ROS) on illumination. One possibility is the physiological stimuli like using pH or oxidative/reductive conditions like described in K. Jeong, C. S. Kang, Y. Kim, Y.-D. Lee, I. C. Kwon, S. Kim, Development of highly efficient nanocarrier-mediated delivery approaches for cancer therapy Cancer Lett. 2016, 374, 31-43; M. H. Staegemann, S. Gräfe, B. Gitter, K. Achazi, E. Quaas, R. Haag, A. Wiehe, Hyperbranched Polyglycerol Loaded with (Zinc-) Porphyrins: Photosensitizer Release Under Reductive and Acidic Conditions for Improved Photodynamic Therapy, Biomacromolecules 2018, 19, 222-238.

Apart from tumor therapy, another field of application for PDT is antibacterial PDT that is the application of photosensitizers and light against localized bacterial infections. Bacteria are generally divided into two main groups based on the different properties and construction of their outer membranes, i.e. Gram-positive and Gram-negative bacteria. For antibacterial PDT other dyes have been employed than for tumor therapy. Whereas for antitumor PDT amphiphilic photosensitizers have proven to be most effective, for antibacterial PDT usually more hydrophilic and water-soluble dyes have been employed. Specifically for Gram-negative bacteria water-soluble positively charged photosensitizers have been used. Also for this field new and effective photosensitizers and respective formulations are needed.

Based on the above, the object of the present invention is to provide an effective carrier, or support, respectively, for biologically active compositions of dyes that can effectively be used as photosensitizer compositions for a wide range of light irradiation treatments such as PDT of cancer, infections and other diseases.

This object is solved at least in part by a polymer having the features of independent claim 1. This object is further at least in part solved by a pharmaceutical composition having the features of independent claim 2, by a method having the features of independent claim 8, by a monomer having the features of independent claim 13, by a polymer having the features of independent claim 14 and by a pharmaceutical composition having the features of independent claim 15. Advantageous embodiments are given in the dependent claims, in the further description as well as in the figures, wherein the described embodiments can, alone or in any combination of the respective embodiments, provide a feature of the present invention unless not clearly excluded. Further, features and advantages as described in respective embodiments can be transferred to further embodiments.

The present invention provides biologically active compositions comprising certain dyes, polymers and auxiliary reagents that can be used as photosensitizers for a wide range of light irradiation treatments such as PDT of cancer, hyperproliferative diseases, dermatological disorders, viral or bacterial infectious diseases, ophthalmological disorders and/or urological disorders, for example. The present invention enhances the effectiveness of biologically active compounds and enhances selectivity for target tissues over healthy surrounding tissues due to its tailored amphiphilicity and custom-made pharmacokinetic behaviour depending on the particular application.

In order to obtain the compositions, the present invention uses photosensitizers such as substituted tetrapyrrole derivatives or other dyes which can be loaded on, incorporated in or attached to a polymer according to the invention. Suitable polymers for the current invention are obtained by polymerization of monomers having a light-cleavable protecting group in side chain. The present disclosure provides methods, such as ring-opening polymerization (ROP) and polycondensation, to prepare light degradable polymers. Preferred examples of suitable polymers for PDT application comprise polycarbonates and polyesters like described below. Preferred light degradable polymers have a degradation period less than 1 day, preferably less than 1 hour under irradiation with UV or visible light.

In particular, described is a polymer, which polymer preferably is effective as carrier for photosensitizers for PDT, wherein the polymer is selected from the group consisting of a) a polycarbonate based on the formula 10

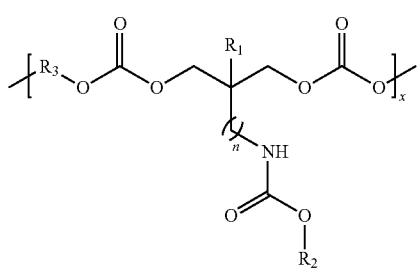

Wherein: n=0 or 1; x=1-1000;
R₁ is: H or an alkyl chain with 1 to 5 carbon atoms;
R₂ is selected from the group consisting of:

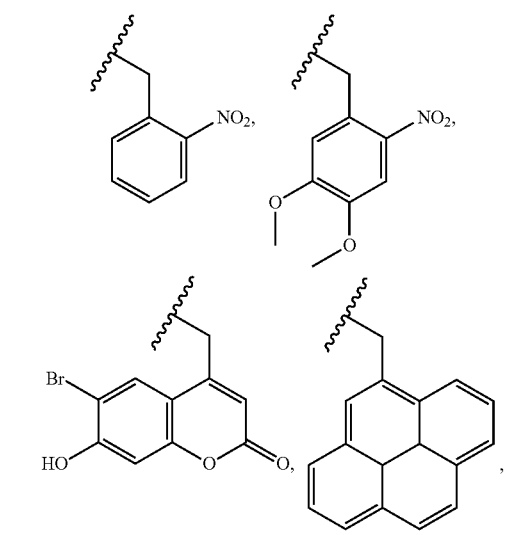

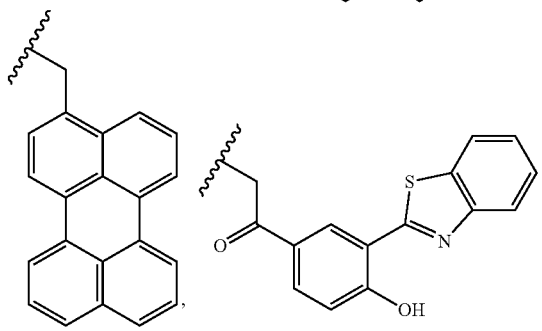

R₃ is: a divalent radical bridging group formed from an alkyl, aryl, or alkylene group having 1 to 10 carbon atoms;

b) a block copolymer based on the formula 12

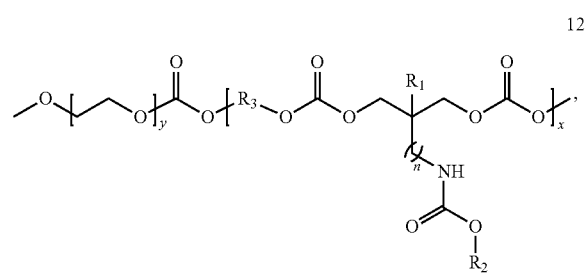

wherein: n=0 or 1; x=1000; y=1-1000;
R₁ is: H or an alkyl chain with 1 to 5 carbon atoms;
R₂ is selected from the groups consisting of:

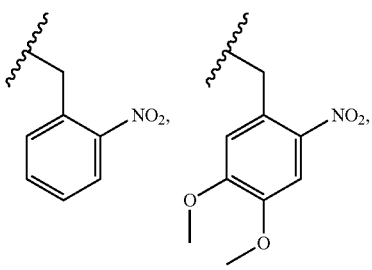

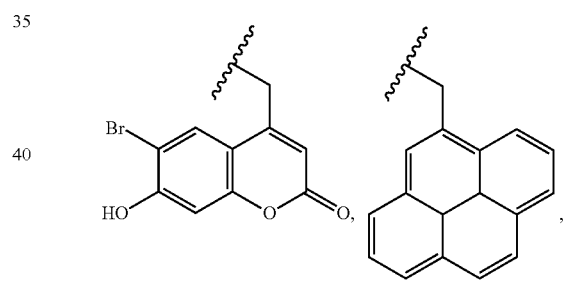

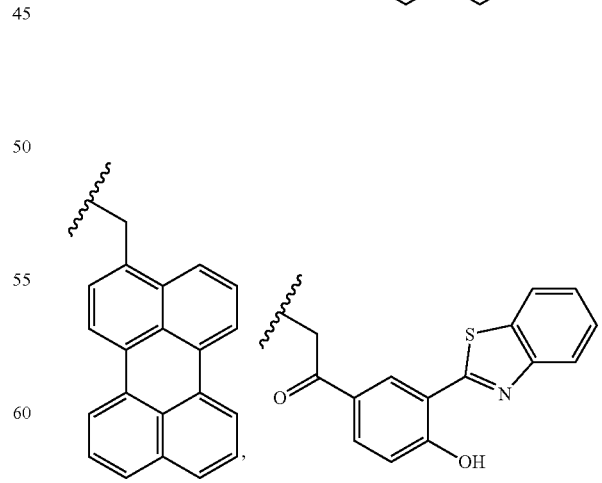

R₃ is: a divalent radical bridging group formed from an alkyl, aryl, or alkylene group having 1 to 10 carbon atoms; and c) a polyester based on the formula 13

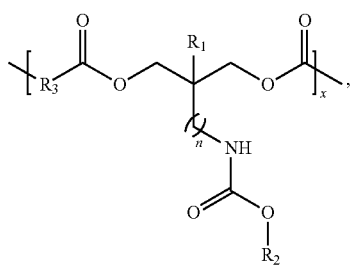

wherein: n=0 or 1; x=1-1000;
$R_1$ is: H or an alkyl chain with 1 to 5 carbon atoms;
$R_2$ is selected from the group consisting of:

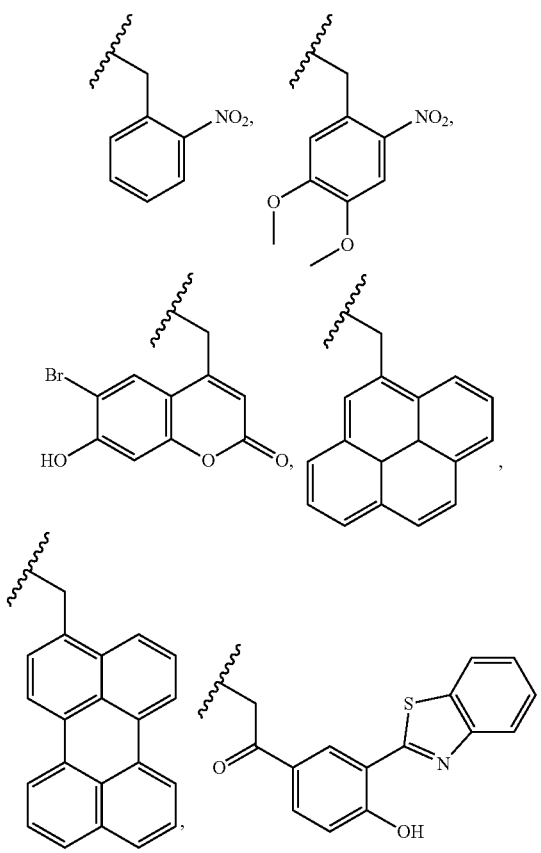

$R_3$ is: formed from an alkyl, aryl, or alkylene group having 1 to 10 carbon atoms.

In each of polymers according to formulae 1, 2 and 3, $R_2$ may particularly be 1,3-propylene, 1,4-butylene, 1,5-pentylene, 1,6-hexylene, 1.4-cyclohexanedimethylene and 1,4-benzenedimethylene groups, and the like.

Further and according to all polymers as described, it may be provided that x is in a range of x=2-1000, such as x=5-1000, for example x=10-1000, such as x=15-1000. According to preferred embodiments, it may further be provided that x is in a range of x=5-100, such as x=2-100, such as x=5-50, for example x=5-40, for example x=5-35, such as x=8-35, for example x=8-30, as a further example x=10-30.

Such a polymer allows in a very effective manner providing a carrier, especially with regard to nanoparticle applications, which may be used in combination with photosensitizers in a photodynamic therapy. Such a polymer especially as a support, or carrier, respectively, thus allows providing biologically active compositions of dyes in combination with polymers that can be used as photosensitizer compositions for a wide range of light irradiation treatments such as PDT of cancer, infections and other diseases. Further, compositions based on such polymers might benefit from the EPR effect.

One of the limitations of current PDT lies in the difficulties of administering the highly lipophilic anti-tumor photosensitizers. Though this can partly be overcome by suitable nanoparticle formulations and carrier systems, which might under circumstances then also benefit from the EPR effect, there is the difficulty of release of the photosensitizer molecule from the carrier system. The compositions disclosed in the current invention and especially the polymer as described above address this problem by providing biocompatible formulations which can be cleaved or degraded by light irradiation thereby releasing the photosensitizer molecules (i.e. dye molecules) at the desired treatment site. The dye molecules thus released can than additionally be activated by light irradiation for photodynamic treatment. In addition due to their light-absorbing and—emitting properties these compounds may also be employed for diagnostic purposes e.g. by detecting their fluorescence.

Therefore, the difficulties of the solutions of the prior art are at least in part overcome in an effective and well controllable manner.

The present invention thus allows to provide formulations for hydrophobic photosensitizers used for photodynamic therapy based on light degradable polymeric material.

Particularly, the polymers as described allow providing polymer particle formulations for hydrophobic photosensitizers of the tetrapyrrole type, namely chlorins and bacteriochlorins based on light-sensitive polycarbonates or polyesters and a stabilizing agent, preferably selected from the group consisting of poly(vinyl alcohol) (PVA), polysorbate, poloxamer, and human serum albumin and the like. Thus, the polymers as described are effective in binding such dyes of the tetrapyrrole type, which due to the effectivity of such dyes is a very beneficial feature especially in combination with photodynamic therapy.

Further, the light-sensitive polymers are cleavable by light in a range of less than 500 nm, which might be especially advantageous for photodynamic therapies. On exposition to light of certain wavelengths the carrier polymers may thus be degraded, thereby releasing dye molecules which can than additionally be activated by light irradiation for photodynamic treatment.

Following the above, further described is a pharmaceutical composition, comprising
  a light-cleavable polymer formed as nanometer particles, wherein the light-cleavable polymer comprises a polymer as described before;
  a therapeutically effective amount of a photosensitizer, such as in an amount of 1 to 500 μg per mg light-cleavable polymer; and
  optionally one or more auxiliary agents, such as a stabilizer.

With regard to the light-cleavable polymer, it is referred to the description as provided above and below with regard to the polymer.

With regard to the photosensitizer, due to high effectivity and effective binding conditions to the polymer, it is preferred that the photosensitizer is tetrapyrrole-based and particularly hydrophobic photosensitizer, wherein it may be especially preferred, that the photosensitizer comprises or is formed of a chlorin or bacteriochlorin derivative according to formula A

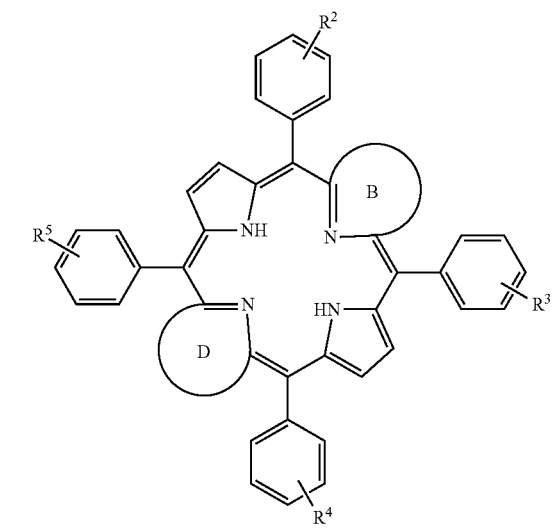

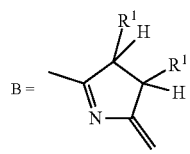

wherein:

R¹ is: H or OH;

R² to R⁵ are different or the same and comprise substituents either in the meta- or para-position of the phenyl ring with R² to R⁵ independently of one another chosen from a group of substituents consisting of: —OH, —COOH, —NH₂, —COOX, —NHX, OX, —NH—Y—COOH, or —CO—Y—NH₂;

wherein:

X is a polyethyleneglycol-residue with $(CH_2CH_2O)_nCH_3$ with n=1-30 or a carbohydrate moiety;

Y is peptides or oligopeptides;

wherein n=1-30; and ring D has the structure:

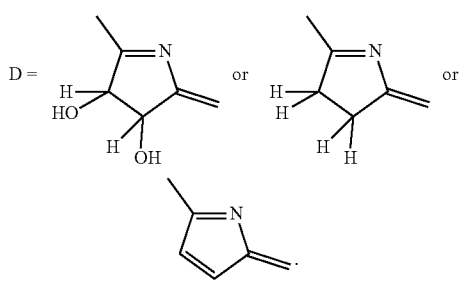

With this regard, it might be especially preferred that the photosensitizer is a tetrapyrrolic compound based on the formulas 14, 15, 16, 17, 18 or 19:

14

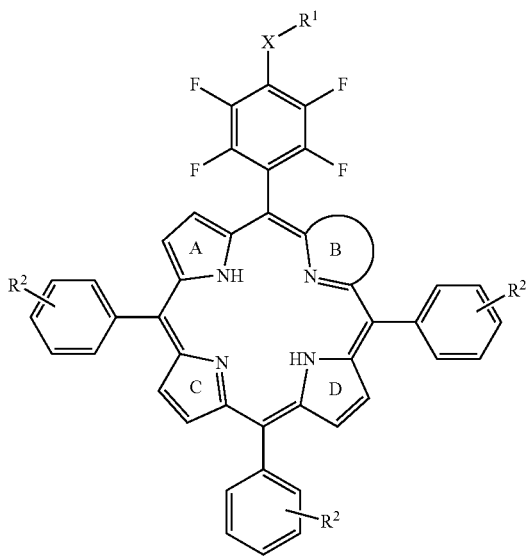

15

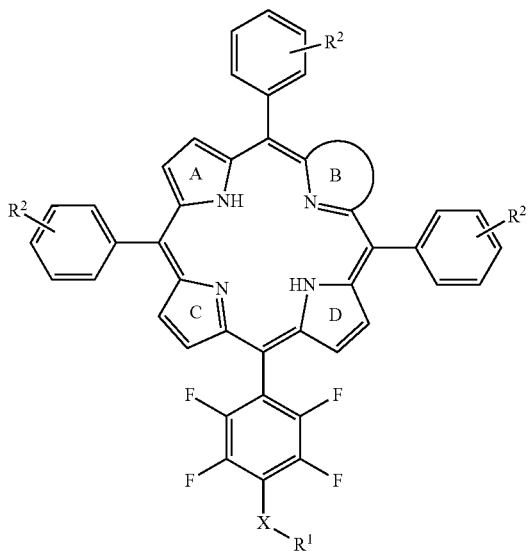

16
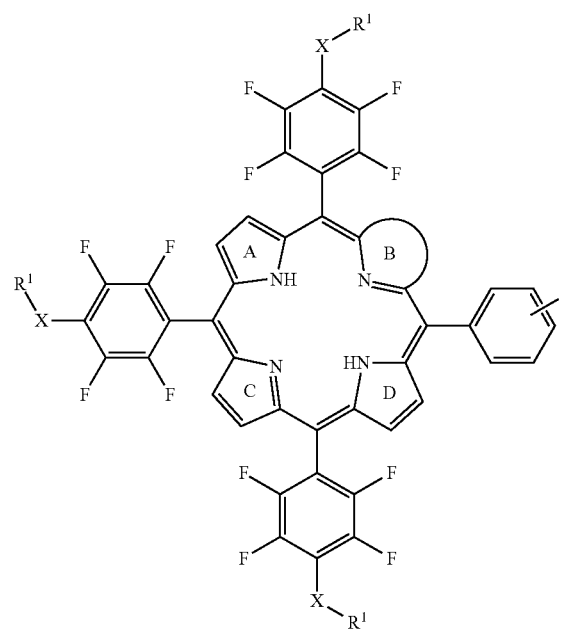
18
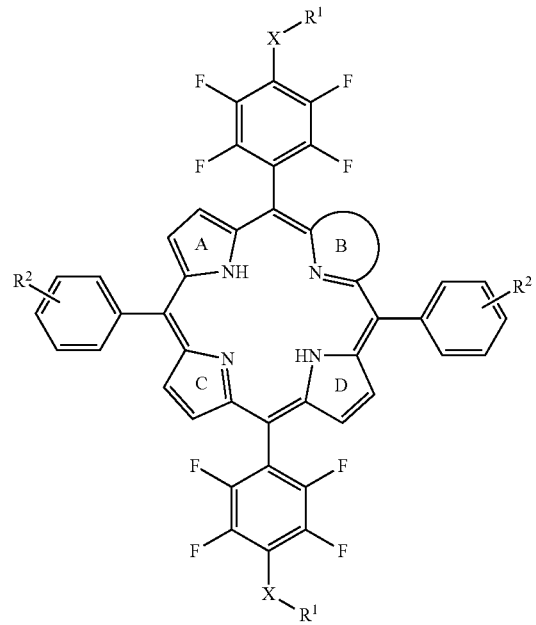
17
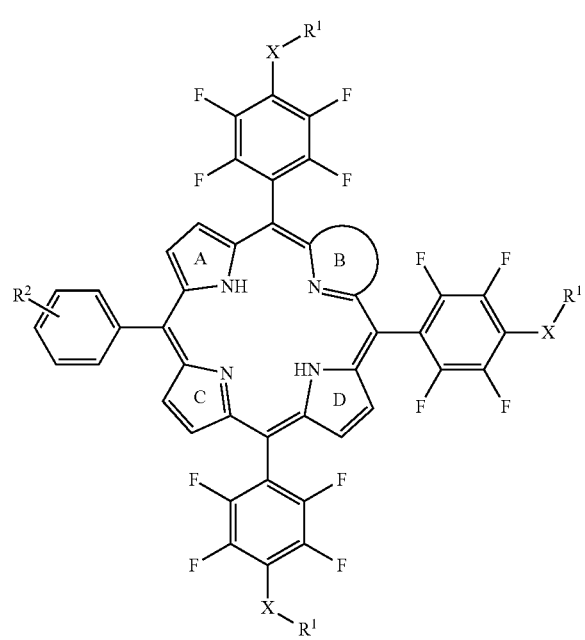
19
wherein:
B is selected from:
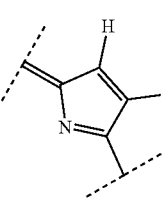 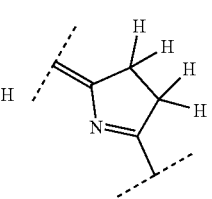 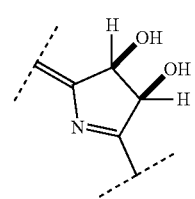

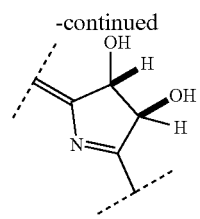

X is: NH, O or S;

R¹ is a linear or branched alkyl chain with 3-4 carbon atoms and containing at least two hydroxyl moieties; wherein R¹ is particularly CH(CH₂OH)₂, CH₂—CH(OH)—CH₂OH, CH(OH)—CH(OH)—CH₃;

R² is: a substituent either in the meta- or para-position of the phenyl ring with R² is —OH, —COOH, —COOY, —NHY, OY, —NH—Z—COOH, or —CO—Z—NH₂; wherein:

Y is a polyethyleneglycol-residue with $(CH_2CH_2O)_nCH_3$ with n=1-30 or a carbohydrate moiety; and Z is selected from peptides or oligopeptides wherein n=1-30.

In a specifically preferred embodiment, the photosensitizer in the composition is 5,10,15,20-tetrakis(3-hydroxyphenyl) chlorin (mTHPC, Temoporfin).

In yet another preferred embodiment the photosensitizers in the composition are those taken from disclosure WO2016/051361A1 by Golf et al.

In yet another preferred embodiment the photosensitizers in the composition are those taken from disclosure WO2010/033678A2 by Wiehe et al.

In yet another preferred embodiment the photosensitizers in the composition are those taken from disclosure WO2013/015774A1 by Aicher et al.

With regard to the stabilizing agent it may be preferred that the latter is selected from the group consisting of polyvinyl alcohol, polysorbate, poloxamer, and albumin, which might be human serum albumin.

The present invention thus provides pharmaceutical nanoparticulate formulations for clinical use in photodynamic therapy comprising a photosensitizer, light-sensitive polymer such as polycarbonates or polyesters and optionally one or more auxiliary reagents such as stabilizers, which are stable in storage and reconstitution. These nanoparticulate formulations provide therapeutically effective amounts of photosensitizer for parenteral, topical or oral/peroral administration. On irradiation with light of suitable wavelengths the carrier polymer of these particles is degraded/cleaved releasing photosensitizer molecules which can then additionally be activated by light irradiation for photodynamic treatment. In particular, tetrapyrrole derivatives can be used as photosensitizers whose efficacy and safety are enhanced by such nanoparticulate formulations.

The present invention allows providing polymer particle formulations for hydrophobic photosensitizers which enable a high variation of photosensitizer loading efficiency, such as in the range of 1 to 500 μg photosensitizer per mg polymer particles, to the particle system giving the opportunity of a high variability in drug pharmacokinetics.

In order to form the polymers as described above which are useful for the pharmaceutical composition as described above for the reasons as described above, respective monomers are required which are as described below and which also form part of the present invention.

Described are thus monomers, usable for forming a polymer according to claim 1, wherein the monomer is selected from the group consisting of a cyclic carbonyl monomer based on the formula 20

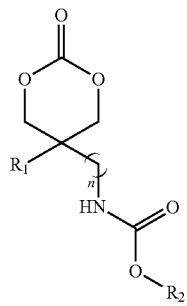

wherein: n=0 or 1

R₁ is: H or an alkyl chain with 1 to 5 carbon atoms

R₂ is selected from the group consisting of:

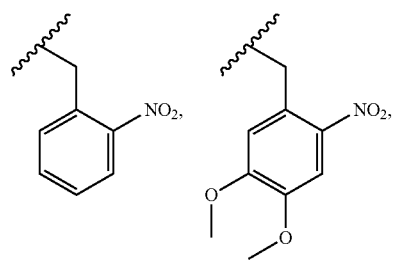

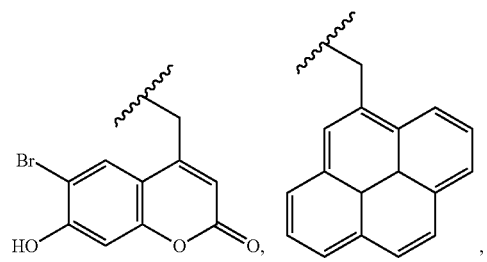

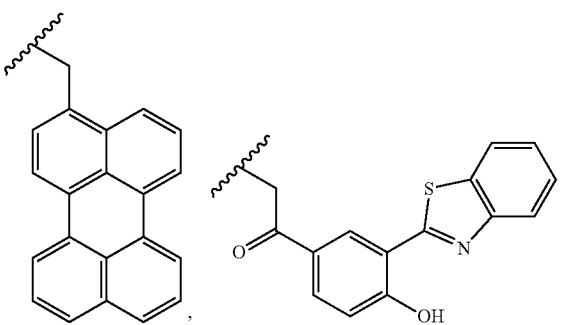

and
a diol monomer based on the formula 21

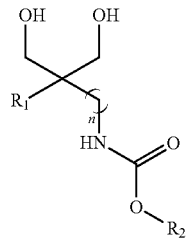
(21)

wherein: n=0 or 1
$R_1$ is: H or an alkyl chain with 1 to 5 carbon atoms
$R^2$ is selected from the group consisting of:

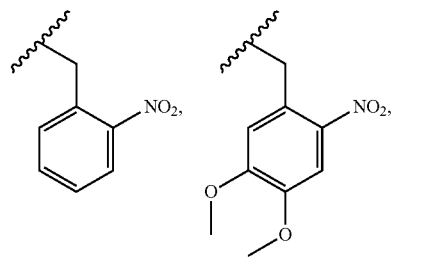

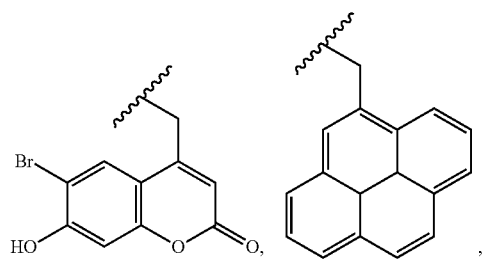

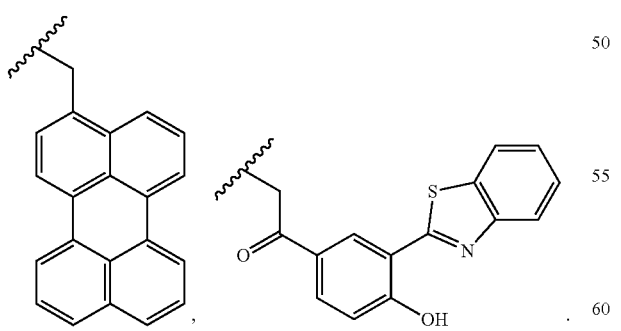

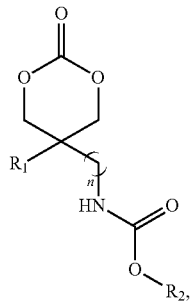
(22)

wherein n is an integer from 0 to 1, and $R_1$ is a substituent comprising H, or an alkyl chain with 1 to 5 carbon atoms, and $R_2$ is a light-cleavable protecting group and selected from:

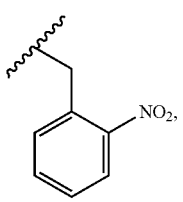
A

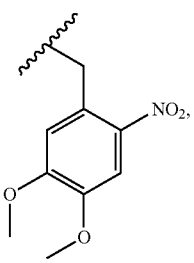
B

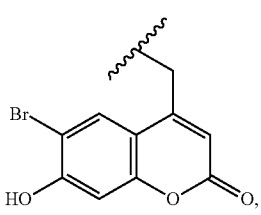
C

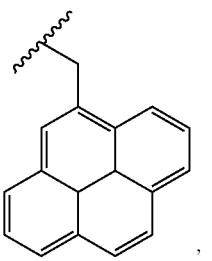
D

In a preferred embodiment cyclic carbonyl monomers can be prepared so that light-cleavable protecting group is attached by a carbamate linkage. The cyclic carbonyl monomers can be selected independently from compounds of the general formula 22:

E

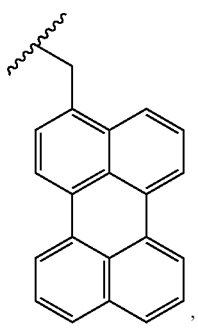

,

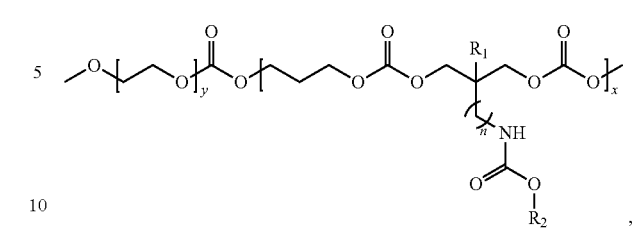

wherein x and y represent the number of repeating units of ethylene glycol and carbonate with x from 1 to 1000 and y from 1 to 1000, respectively, and n is an integer from 0 to 1, and $R_1$ is a substituent comprising H or an alkyl chain with 1 to 5 carbon atoms, and $R^2$ is a light-cleavable protecting group.

In another embodiment, diol monomers attached with light-cleavable protecting group by a carbamate linkage capable of polycondensation have the general formula 25:

F

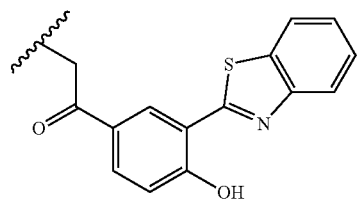

, wherein n is an integer from 0 to 1, and $R_1$ is a substituent comprising H or an alkyl chain with 1 to 5 carbon atoms, and $R_2$ is a light-cleavable protecting group.

and the light-cleavable protecting groups have absorption maxima ($\lambda_{max}$) of $\lambda_{max}$ (A)=265 nm, $\lambda_{max}$(B)=346 nm, $\lambda_{max}$ (C)=370 nm (one-photo process) or 740 nm (two-photo process), $\lambda_{max}$ (D)=520 nm, $\lambda_{max}$(E)=365 nm and $\lambda_{max}$ (F)=420 nm.

In another preferred embodiment of the present invention light degradable polycarbonates can be prepared by ring-opening polymerization (ROP) of 1,3-dioxan-2-one (TMC) and a cyclic carbonyl monomer with formula 10 catalyzed by 1,8-diazabicyclo(5.4.0) undec-7-ene (DBU). The light degradable polycarbonates prepared by ROP are based on the general formula 23:

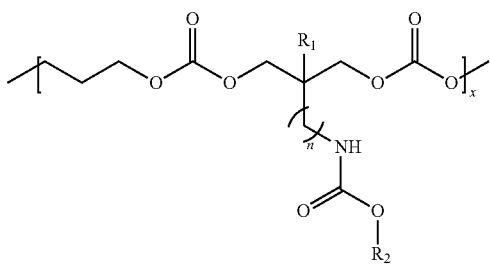

, wherein x represents the number of repeating units from 1 to 1000, and n is an integer from 0 to 1, and $R_1$ is a substituent comprising H or an alkyl chain with 1 to 5 carbon atoms, and $R^2$ is a light-cleavable protecting group.

In another embodiment, the polymers used in the present invention may also be PEGyated polycarbonate block copolymer, poly(ethylene glycol) methyl ether-block-polycarbonate (PC-PEG), obtained by ROP using poly(ethylene glycol) methyl ether as initiator. The light degradable PC-PEGs have the general formula 24:

In a specifically preferred embodiment, light degradable polycarbonates can be prepared by two-step polycondensation of an aliphatic or aromatic diol and a diol having structure of formula 14 with diphenylcarbonate or triphosgene. More specific aliphatic or aromatic diols include 1,4-butanediol 1 (BD), 1,5-pentanediol (PD), 1,6-hexanediol (HD), 1,4-cyclohexanedimethanol (CDM) and 1,4-benzenedimethanol (BDM). The light degradable polycarbonates prepared by polycondensation are based on the general formula 26:

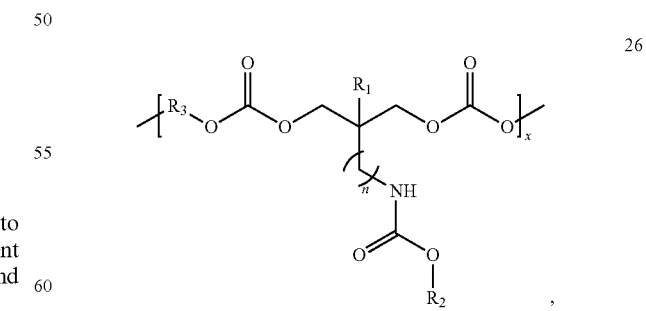

, wherein x represents the number of repeating units from 1 to 1000, and n is an integer from 0 to 1, and $R_1$ is a substituent comprising H or an alkyl chain with 1 to 5 carbon atoms, and $R_2$ is a light-cleavable protecting group, and $R_3$ is a divalent radical bridging group selected from 1,4-butylene, 1,5- pentylene, 1,6-hexylene, 1,4-cyclohexanedimethylene and 1,4-benzenedimethylene groups, and the like.

In another embodiment, the present invention provides methods for the preparation of light degradable polyesters by polycondensation of a diacyl chloride with a diol having structure of formula 14. The diacyl chloride is selected from the group consisting of adipoyl chloride (AC), succinyl chloride (SC) and terephthaloyl chloride (TC). The general structure of the light degradable polyesters is shown below as formula 27:

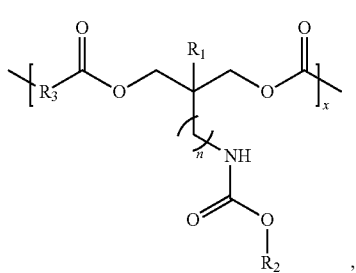

wherein x represents the number of repeating units from 1 to 1000, and n is an integer from 0 to 1, and $R_1$ is a substituent comprising H or an alkyl chain with 1 to 5 carbon atoms, and $R_2$ is a light-cleavable protecting group, and $R_3$ is a divalent radical bridging group selected from 1,2-ethylene, 1,4-butylene and 1,4-benzylene groups, and the like.

The light-sensitive protecting groups in formula 23, 24, 26 and 27 can be removed under irradiation with UV or visible light and free amine groups can be formed in polymer side chains. Polymer chains can be degraded by intramolecular cyclization of the free amine groups with ester groups in the backbone leading to rapid drug release.

The invention provides methods to prepare formulations of light-cleavable photosensitizer-containing nanoparticles preferably using photosensitizers of the chlorin and bacteriochlorin type like described in more detail below. The nanoparticles prepared by the methods disclosed below have a predictable size and uniformity (in size distribution). Preferred light-cleavable nanoparticles have a mean size less than 500 nm, preferably less than 200 nm, wherein the minimum size may be due to the formulation process and/or may lie at 50 nm, for example. The term "diameter" is not intended to mean that the nanoparticles have necessarily a spherical shape. The term refers to the approximate average width of the nanoparticles.

In a preferred embodiment of the present invention, the light-cleavable nanoparticles can be prepared so that the photosensitizer loading can be varied in a wide concentration range, such as 1 to 500 μg photosensitizer per mg nanoparticles.

In a specifically preferred embodiment of the present invention, the light-cleavable nanoparticles can be prepared so that the photosensitizer is attached by incorporation in the particle matrix, is attached by adsorption to the particle matrix or is attached by incorporation in and adsorption to the particle matrix, resulting in a high variability of drug loading characteristics.

Drug targeting effectiveness of present nanoparticle systems may be enhanced with one or more ligands such as antibodies, peptides or receptor-ligands bound to light-cleavable nanoparticles, maintaining the photosensitizer chemical entity by not bounding to photosensitizer molecules.

The nanoparticles of the invention may be dehydrated for improved stability on storage. The preferred method of dehydration is freeze-drying or lyophilisation. Optionally, a lyoprotectant may be used as an additive to improve the stability during the freeze-drying and during reconstitution in an aqueous medium.

With regard to the formation of a pharmaceutical composition like described above, described is a method, comprising the following steps.

Firstly, according to step a) the method comprises the step of dissolving the light-cleavable polymer alone or in combination with a further polymer, such as selected from the group consisting of typical nanoparticle forming polymers such as Poly(lactid-co-glycolid) (PLGA), Polylactide (PLA), Polyethyleneglycole-Poly(lactid-co-glycolid) (PEG-PLGA), Polyethyleneglycole-Polylactide PEG-PLA in an organic solvent to form a polymer solution.

In particular, using nanoparticle forming polymers may enhance the properties with regard to light cleavage in case such nanoparticulate forming polymers are added to the organic solvent. Further, with regard to step a) it may be realized that the organic solvent used in step a) may be a water-miscible solvent, such as acetone, or water immiscible solvents such as dichloromethane.

According to step b), the method comprises the optional step of dissolving stabilizer in an aqueous solution to form an aqueous stabilizing solution.

Further and according to optional step c) the method comprises the step of filtering said polymer solution and optionally said stabilizing solution through a filtration unit. This optional step may enhance the size unity of the formed particles.

According to method step d), the method comprises the step of mixing the optionally filtered polymer solution with an aqueous solution, such as with the optionally filtered stabilizing solution, to form nanoparticles. This step particularly may be performed under high shear mixing, to form either an organic solvent-water solution or an oil-in-water nanoemulsion wherein a high shear mixing may e.g. be realized by using so-called Ultra-Turrax systems having a high rotational speed, such as 24000 rpm and/or using mixing times, such as for example 30 minutes. The nanoparticles are formed spontaneously due to the changing solvation properties of the solution by adding the aqueous solution to the organic solution, or vice versa, especially in case the organic phase is solved in the aqueous phase. In case an emulsion is formed, the particles are formed in the organic phase in case the latter is removed such as by evaporation.

According to the above, it is provided that according to step e), the organic solvent is evaporated. In particular, the organic solvent and preferably the aqueous solution is removed from the nanoparticles especially by means of evaporation especially under stirring in order to form the nanoparticles or to remove the solvent from the nanoparticles, respectively.

Further and according to step f), it is provided that the method comprises the step of purifying the formed nanoparticles, especially by using water or the formed stabilizing aqueous solution, such as generally including polyvinylalcohol, such as by a rinsing steps.

Further and according to step g), the method comprises the step of adding photosensitizer to the solution formed in step a) or to the purified nanoparticles formed in step f), especially to achieve incorporative and adsorptive binding, or to the purified nanoparticles formed in step f) in order to achieve solely adsorptive binding on particle surface.

It may be preferred that the formed composition especially after step g) is freeze dried in the presence of cryoprotective agents, wherein the latter may for example selected from the group consisting of glucose, trehalose, sucrose, sorbitol, mannitol and combinations thereof. Like stated above, this may show significant advantages with regard to long term stability.

The present invention thus provides methods for the use of nanoparticle photosensitizer formulations based on light-cleavable polymers in photodynamic therapy, comprising the administration of the nanoparticles, their accumulation in the target tissue, the induction of drug release from the nanoparticles by light-irradiation and the activation of the photosensitizer by light of a specific wavelength.

Given the above, the present invention relates to polymers or pharmaceutical formulations like described before including derivatives thereof for use in the preparation of a medicament, in particular for use in the preparation of a medicament for photodynamic therapy.

In particular, the present invention relates to polymers or pharmaceutical formulations like described above including derivatives thereof for forming a medicament for use in the photodynamic therapy such as of tumors and other neoplastic diseases, and related conditions, of dermatological disorders, ophthalmological disorders or urological disorders, and related conditions arthritis and similar inflammatory diseases, and related conditions, in particular for the respective clinical use.

The administration of the nanoparticles is preferably by parenteral means such as, but not limited to, intravenous injection. Furthermore the nanoparticles may be administered by topical application on skin and mucosa or by oral/peroral application, particularly enabling a mucus-penetration on mucous membranes.

The present invention thus allows providing nanoparticle formulations for hydrophobic photosensitizers which enable the attachment of drug targeting ligands to the nanoparticle surface and thus an effective drug transport to target cells and tissues combined with a drug release after cellular accumulation.

It may further be allowed to provide methods for the production of light-sensitive polycarbonates and polyesters which enable a light degradation under irradiation with UV or visible light. The light-sensitive polymers of the present invention are stable at room temperature at air for long-term storage.

A further advantage of the present invention is the provision of methods for the production of light-cleavable, photosensitizer-loaded nanoparticles of a mean particle size less than 500 nm, with the photosensitizers being chlorins or bacteriochlorins. The nanoparticles of the present invention are stable enough to allow freeze drying and reconstitution in an aqueous medium.

It further becomes clear that the present invention provides methods for the use of said nanoparticle photosensitizer formulations in photodynamic therapy for the treatment of tumors and other neoplastic diseases, dermatological disorders, ophthalmological disorders, urological disorders, arthritis and similar inflammatory diseases, viral or bacterial infections, ophthalmological disorders, not being restricted hereto.

Further, the present invention provides light-sensitive polycarbonates and polyesters that can effectively load hydrophobic drug during nanoparticle formulations and rapidly release drug under irradiation with UV or visible light. With this regard, light-cleavable nanoparticles are provided that can be administered by the parenteral route, by topical application, or by oral/peroral application, particularly enabling a mucus-penetration on mucous membranes.

Apart from that, the present invention provides pharmaceutically acceptable formulations to be injected avoiding undesirable effects like precipitation at the injection site or delayed pharmacokinetics of the compounds.

These and other aspects of the invention will be apparent from and elucidated with reference to the figures and examples described hereinafter, wherein even individual features disclosed in the figures and the examples and in the disclosure as a whole can constitute an aspect of the present invention alone or in combination, wherein additionally, features of different embodiments can be carried over from one embodiment to another embodiment without leaving the scope of the present invention.

Figure 1:
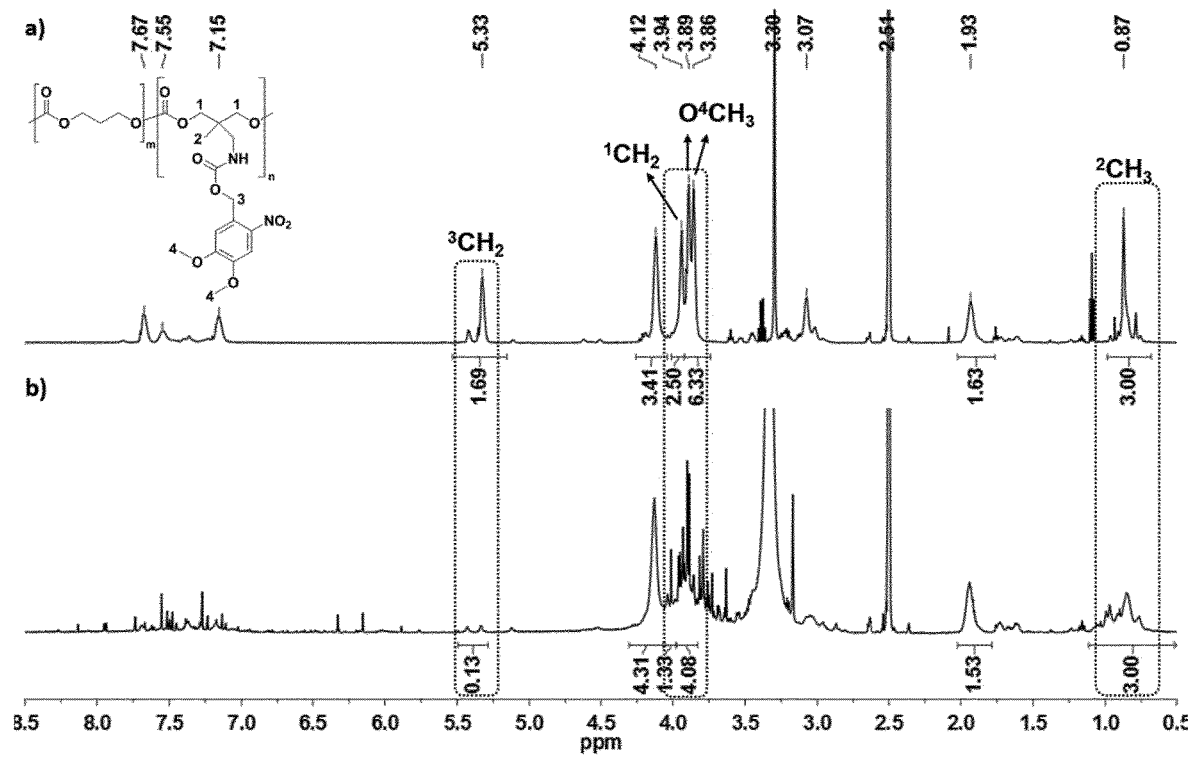
FIG. 1 shows (a) 1H NMR spectrum of PC01 in DMSO-$d_6$ before irradiation and (b) $^1$H NMR spectrum of PC01 in DMSO-do after irradiation with UV light (320-480 nm, 0.603 W/cm$^2$) for 15 min.

The following examples are presented to provide those of ordinary skill in the art with a full and illustrative disclosure and description of how to make the biologically active compositions of the invention and show their photodynamic activity and are not intended to limit the scope of what the inventor regards as the invention. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

EXAMPLES

Materials for Monomer and Polymer Synthesis and Characterization

All reagents were used as purchased from commercial suppliers. Benzyl alcohol (BnOH) (99%, Acros Organics) was distilled over calcium hydride and stored under Ar atmosphere. Dichloromethane (DCM) (98%, Stockmeier Chemie) was dried over $CaCl_2$) then distilled over calcium hydride. Tetrahydrofuran (THF) (98%, Stockmeier Chemie) was dried over KOH then distilled over calcium hydride. 1,3-dioxan-2-one (TMC) (99%, Shanghai Worldyang Chemical Co.) was purified by column chromatography with ethyl acetate/n-hexane (3:1).

$^1$H and $^{13}$C nuclear magnetic resonance (NMR) spectra were recorded using Bruker AV 500 spectrometer at 500 MHz and 125 MHz, respectively. Chloroform-d ($CDCl_3$-d, 99.8 D %) or dimethylsulfoxide-d$_6$ (DMSO-d$_6$, 99.8 D %) were used as solvent for NMR measurements. ESI-ToF-mass spectra were measured on a SYNAPT G2 HDMS™ from Waters. The mass spectrometric parameters were the following: capillary voltage: 3 kV; sampling cone voltage: 45 V; extraction cone voltage: 1.7 V; cone gas flow: 30 L/h; source temperature: 120° C.; desolvation gas flow: 650 L/h; desolvation temperature: 350° C.; helium cell gas flow: 180 mL/min. The sample was dissolved in acetonitrile (2 g/L) and then mixed with NaI 0.1 g/L in methanol and methanol in the ratio of 5:5: 990. Data were obtained with Mass Lynx 4.1. Light degradation experiments were performed using an OmniCure S1500 Curing System from Lumen Dynamics with a power of 0.607 W/cm$^2$ (320 to 480 nm). UV/VIS spectra were recorded on Specord 50 PLUS UV-VIS spectrophotometer from Analytik Jena using Aspect UV 1.1 software. The molar masses and dispersities (ÐM) were analyzed employing an advanced polymer chromatography (APC) system equipped with two consecutive columns (Acquity APC XT columns filled with polyethoxysilane with a defined porosity of 125 Å and 45 Å, respectively) and an Acquity APC RI-detector. The system was operated at a flow rate of 0.7 mL/min with THF/DMF (v/v=80/20) as solvent. Poly(methyl methacrylate) (PMMA) standards were used for calibration.

Example 1a

Synthesis of Cyclic Carbonyl Monomer with Light-Cleavable Protecting Group

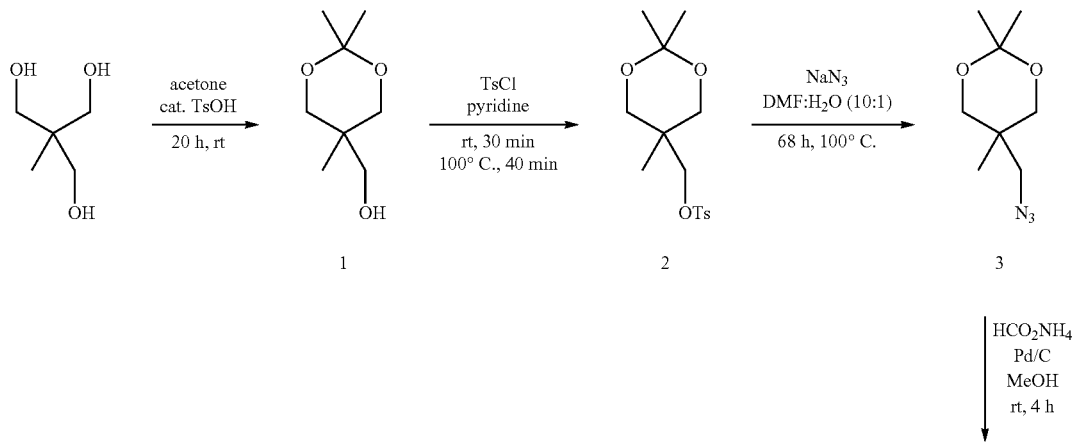

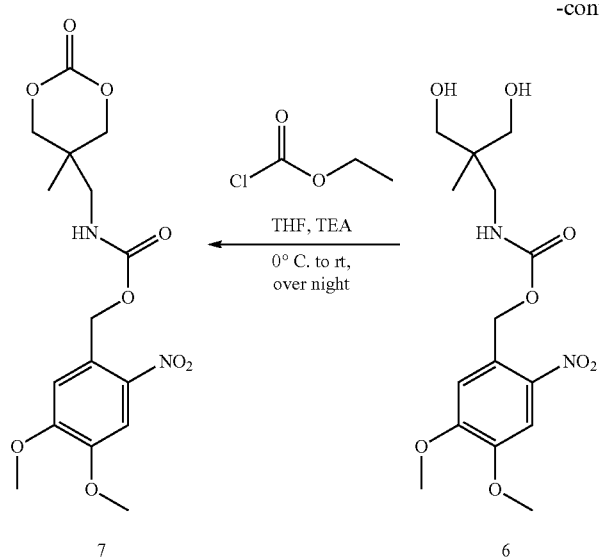
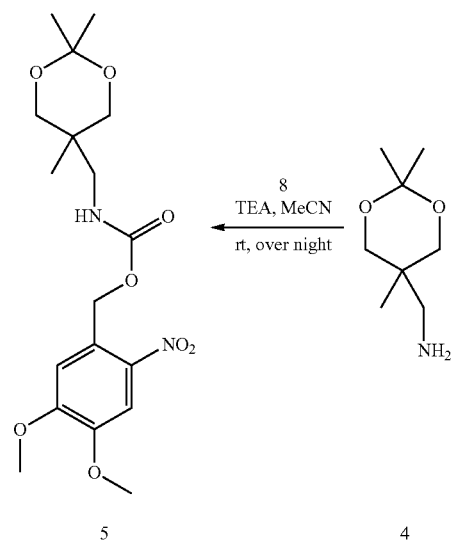

Synthesis of (2,2,5-trimethyl-1,3-dioxan-5-yl) methanol (1)

1 was synthesized according to the literature, see Z. Jia, D. E. Lonsdale, J. Kulis, and M. J. Monteiro, Construction of a 3-Miktoarm Star from Cyclic Polymers, ACS Macro Lett., 2012, 1, 780-783.

In a round bottom flask 80 g 2-(hydroxymethyl)-2-methylpropane-1,3-diol (0.67 mol), 320 mL dry acetone, and 100 mg p-toluenesulfonic acid monohydrate (TsOH·H$_2$O) (0.53 mmol) were stirred overnight at room temperature. The reaction was quenched by addition of 150 µL triethylamine (TEA) (1.1 mmol). The organic solvent was removed under reduced pressure and the residue was taken up in 200 mL DCM. The precipitate was filtered off, the DCM was removed under reduced pressure, and the residue was distilled at 0.2 mbar to achieve 86 g of a slightly viscous liquid. Yield: 81%

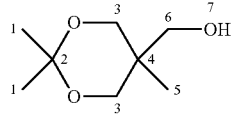

$^1$H-NMR (500 MHZ, CDCl$_3$): δ (ppm)=0.81 (s, 3H, $^5$CH$_3$), 1.37 (s, 3H, $^1$CH$_3$), 1.42 (s, 3H, $^1$CH$_3$), 2.47 (b, 1 H, $^7$OH), 3.58 (m, 2H, $^3$CH$_2$), 3.64 (m, 2H, $^3$CH$_2$), 3.66 (s, 2H, $^6$CH$_2$).

$^{13}$C-NMR (125 MHz, CDCl$_3$): δ (ppm)=17.70 (1 C, $^5$CH$_3$), 20.33 (1 C, $^1$CH$_3$), 27.33 (1 C, $^1$CH$_3$), 34.87 (1 C, $^4$C$_q$), 66.01 (1 C, $^6$CH$_2$), 66.46 (2 C, $^3$CH$_2$), 98.10 (1 C, $^2$C$_q$).

Synthesis of (2,2,5-trimethyl-1,3-dioxan-5-yl) methyl-4-methylbenzenesulfonate (2)

2 was synthesized according to the literature. see V. W. Gash, Dienoalkyl ethers. General synthesis of the symmetrical ethers, J. Org. Chem., 1972, 37, 2197-2201.

A solution of 108 g 4-toluenesulfonyl chloride (TsCl) (0.57 mol) in 140 mL pyridine was dropped over 30 min to a solution of 86.26 g of 1 (0.54 mol) in 270 mL pyridine. The resulting solution was stirred for 40 min at 100° C., cooled and poured in an excess of ice water. The precipitate was collected, washed with water and dried in vacuo to yield 140 g of an off-white solid. The crude product was used without further purification in the next step. Yield: 83%

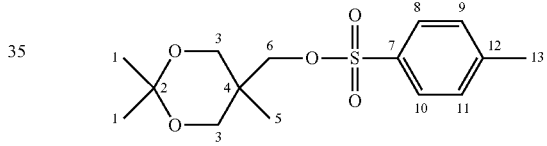

$^1$H-NMR (500 MHZ, CDCl$_3$): δ (ppm)=0.81 (s, 3H, $^5$CH$_3$), 1.22 (s, 3H, $^1$CH$_3$), 1.36 (s, 3H, $^1$CH$_3$), 2.43 (s, 3H, $^{13}$CH$_3$), 3.54 (s, 4H, $^3$CH$_2$), 4.07 (s, 2H, $^6$CH$_2$), 7.34 (d, $^3$J$_{HH}$=8.3 Hz, 2 H, $^{9,11}$CH), 7.79 (d, $^3$J$_{HH}$=8.3 Hz, 2 H, $^{8,10}$CH).

$^{13}$C-NMR (125 MHz, CDCl$_3$): δ (ppm)=17.34 (1 C, $^5$CH$_3$), 19.50 (1 C, $^1$CH$_3$), 21.72 (1 C, $^{13}$CH$_3$), 27.71 (1 C, $^1$CH$_3$), 34.06 (1 C, $^4$C$_q$), 65.65 (2 C, $^3$CH$_2$), 72.61 (1 C, $^6$CH$_2$), 98.18 (1 C, $^2$C$_q$), 128.18 (2 C, $^{8,10}$CH), 129.94 (2 C, $^{9,11}$CH), 132.85 (1 C, $^7$C$_q$), 144.87 (1 C, $^{12}$C$_q$).

Synthesis of 5-(azidomethyl)-2,2,5-trimethyl-1,3-dioxane (3)

3 was synthesized according to the literature, see S. T. Liu and C. Y. Liu, Synthesis of amino-containing phosphines. The use of iminophosphorane as a protecting group for primary amines, J. Org. Chem., 1992, 57, 6079-6080.

37.72 g of 2 (120 mmol), 23.41 g sodium azide (360 mmol), 20 mL water and 200 mL dimethylformamide (DMF) were stirred at 100° C. for 68 h. The mixture was poured in water and extracted 4× with 130 mL diethyl ether. The organic phase was dried over anhydrous MgSO$_4$ and removed under reduced pressure. The residue was purified by column chromatography with 100 g silica gel and ethyl acetate/n-hexane (1:4) to give 20.9 g of a colorless liquid. Yield: 94%

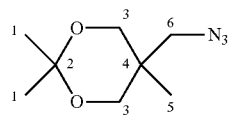

$^1$H-NMR (500 MHZ, CDCl$_3$): δ (ppm)=0.81 (s, 3H, $^5$CH$_3$), 1.38 (s, 3H, $^1$CH$_3$), 1.41 (s, 3H, $^1$CH$_3$), 3.50 (s, 2H, $^6$CH$_2$), 3.57 (m, 4H, $^3$CH$_2$).

$^{13}$C-NMR (125 MHz, CDCl$_3$): δ (ppm)=18.13 (1 C, $^5$CH$_3$), 19.81 (1 C, $^1$CH$_3$), 27.73 (1 C, $^1$CH$_3$), 34.55 (1 C, $^4$C$_q$), 56.14 (1 C, $^6$CH$_2$), 66.78 (2 C, $^3$CH$_2$), 98.22 (1 C, $^2$C$_q$).

Synthesis of (2,2,5-trimethyl-1,3-dioxan-5-yl)methanamine (4)

4 was synthesized similar to the literature, see A. D. Ure, I. A. Lázaro, M. Cottera and A. R. McDonald, Synthesis and characterisation of a mesocyclic tripodal triamine ligand Org. Biomol. Chem., 2016, 14, 483-494.

9.26 g of 3 (50 mmol) and 12.6 g ammonium formate (200 mmol) were dissolved in 130 mL dry methanol. The solution was purged with Ar for 20 min. The freshly degassed mixture was held under Ar atmosphere while 0.9 g Pd/C (10%) was added. The reaction mixture was stirred at room temperature in the opened reaction vessel. After a few minutes the solution became slightly warm and a large gas formation was noticed. From now the reaction mixture was stirred at room temperature for further 4.5 h. Pd/C was removed by a pad of Celite and the solvent was removed under reduced pressure. The residue was taken up in 25 mL water and the resulting solution was extracted 3× with 50 mL diethyl ether. The aqueous phase was basified with 25 g KOH and extracted 5× with 25 mL MeCN. The organic phase was dried over anhydrous MgSO$_4$ and removed under reduced pressure to yield 5.91 g of a colorless liquid. Yield: 74%

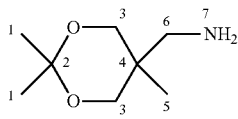

$^1$H-NMR (500 MHZ, CDCl$_3$): δ (ppm)=0.78 (s, 3H, $^5$CH$_3$), 1.21 (b, 2 H, $^7$NH$_2$), 1.36 (s, 3H, $^1$CH$_3$), 1.40 (s, 3H, $^1$CH$_3$), 2.76 (s, 2H, $^6$CH$_2$), 3.58 (m, 4H, $^3$CH$_2$).

$^{13}$C-NMR (125 MHz, CDCl$_3$): δ (ppm)=18.03 (1 C, $^5$CH$_3$), 21.12 (1 C, $^1$CH$_3$), 26.61 (1 C, $^1$CH$_3$), 34.34 (1 C, $^4$C$_q$), 46.41 (1 C, $^6$CH$_2$), 67.34 (2 C, $^3$CH$_2$), 97.96 (1 C, $^2$C$_q$).

Synthesis of 4,5-dimethoxy-2-nitrobenzyl((2,2,5-trimethyl-1,3-dioxan-5-yl)methyl) carbamate (5)

A mixture of 2.954 g of 4 (18.55 mmol), 5.965 g of 8 (15.77 mmol), 4.9 mL TEA (35.16 mmol), and 120 mL dry MeCN was stirred at room temperature overnight. After adding 100 mL DCM the organic phase was washed 2× with 100 mL 0.1 M Na$_2$CO$_3$ solution and 2×with 100 mL 0.3 M NaCl solution. The organic phase was dried over anhydrous MgSO$_4$ and removed under reduced pressure to yield 7.68 g of a viscous yellow liquid. The crude product was used without further purification in the next step. Yield: 84%

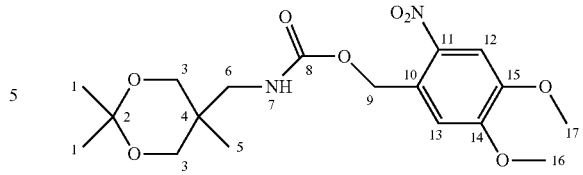

$^1$H-NMR (500 MHZ, CDCl$_3$): δ (ppm)=0.81 (s, 3H, $^5$CH$_3$), 1.40 (s, 3H, $^1$CH$_3$), 1.43 (s, 3H, $^1$CH$_3$), 3.40 (d, $^3$J$_{HH}$=6.1 Hz, 2 H, $^6$CH$_2$), 3.60 (m, 4H, $^3$CH$_2$), 3.95 (s, 3H, O$^{16}$CH$_3$), 3.97 (s, 3H, O$^{17}$CH$_3$), 5.22 (b, 1 H, $^7$NH), 5.52 (s, 2H, $^9$CH$_2$), 7.01 (s, 1H, $^{13}$CH), 7.71 (s, 1H, $^{12}$CH).

Synthesis of 4,5-dimethoxy-2-nitrobenzyl (3-hydroxy-2-(hydroxymethyl)-2-methyl-propyl) carbamate (6)

To a mixture of 5.465 g of 5 (13.70 mmol), 25 mL THF and 25 mL 1 N HCl was added. The suspension was stirred at room temperature overnight. After addition of 100 mL DCM the mixture was washed 3× with 100 mL 0.1 M Na$_2$CO$_3$ solution and 2× with 100 mL 0.3 M NaCl solution. The organic phase was dried over anhydrous MgSO$_4$ and evaporated under reduced pressure.

Purification method 1: diethyl ether was added to the crude product and stirred/triturated until a fine precipitate appears. A large excess of diethyl ether was reduced before the precipitate was collected by filtration and dried in vacuo to achieve 4.326 g of a yellow solid. Yield: 88% Purification method 2: The crude product was purified by column chromatography with silica gel and ethyl acetate to give 4.410 g of a yellow solid. Yield: 90%

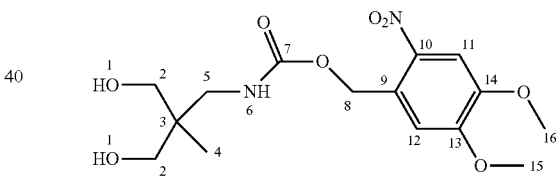

$^1$H-NMR (500 MHz, DMSO-d$_6$): δ (ppm)=0.73 (s, 3H, $^4$CH$_3$), 2.98 (d, $^3$J$_{HH}$=6.3 Hz, 2 H, $^5$CH$_2$), 3.21 (d, $^3$J$_{HH}$=5.5 Hz, 4 H, $^2$CH$_2$), 3.87 (s, 3H, O$^{15}$CH$_3$), 3.91 (s, 3H, O$^{16}$CH$_3$), 4.32 (t, $^3$J$_{HH}$=5.5 Hz, 2 H, $^1$OH), 5.34 (s, 2H, $^8$CH$_2$), 7.19 (s, 1H, $^{12}$CH), 7.22 (t, $^3$J$_{HH}$=6.2 Hz, 1H, $^6$NH), 7.70 (s, 1H, $^{11}$CH).

$^{13}$C-NMR (125 MHz, DMSO-d$_6$): δ (ppm)=17.08 (1 C, $^4$CH$_3$), 41.36 (1 C, $^3$C$_q$), 44.29 (1 C, $^5$CH$_2$), 56.22 (1 C, O$^{15}$CH$_3$), 56.32 (1 C, O$^{16}$CH$_3$), 62.44 (1 C, $^8$CH$_2$), 64.55 (2 C, $^2$CH$_2$), 108.32 (1 C, $^{11}$CH), 110.64 (1 C, $^{12}$CH), 128.11 (1 C, C$_q$), 139.43 (1 C, $^{10}$C$_q$), 147.85 (1 C, $^{13}$C$_q$), 153.48 (1 C, $^{14}$C$_q$), 156.55 (1 C, $^7$C$_q$).

ESI-ToF-MS (m/z): [M+Na]$^+$ calculated for C$_{15}$H$_{22}$N$_2$O$_8$, 381.1274; found, 381.1271.

Synthesis of 4,5-dimethoxy-2-nitrobenzyl ((5-methyl-2-oxo-1,3-dioxan-5-yl)methyl)-carbamate (7)

4.132 g of 6 (11.53 mmol) was suspended in 30 mL anhydrous THF under Ar atmosphere and cooled to 0° C. Subsequently, 4.22 mL TEA (30.45 mmol) and 2.55 mL ethyl chloroformate (26.65 mmol) were added and the suspension was stirred at room temperature for 24 h. The precipitate was collected, washed with 100 mL THF, stirred in 100 mL dest. water for 30 min, filtered off, washed 2× with 100 mL water and 3× with 100 mL diethyl ether, and dried in vacuo to afford 4.011 g of an off-white solid. Yield: 73% atmosphere. The solution was stirred at room temperature for 1.5 h and diluted with 90 mL DCM. After stirring at room temperature overnight the solvent was removed under reduced pressure. The resulting crude product was heated at 85° C. in 290 mL ethanol for 45 min until a fine precipitate was formed. The precipitate was collected and dried in vacuo to afford 14.16 g of a yellowish solid. Yield: 91%

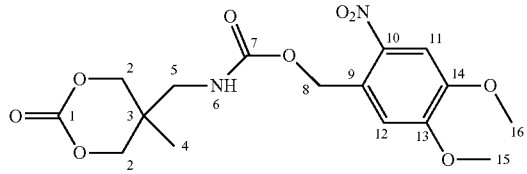 [SMILES: COc1cc(COC(=O)NCC2(C)COC(=O)OC2)c([N+](=O)[O-])cc1OC]

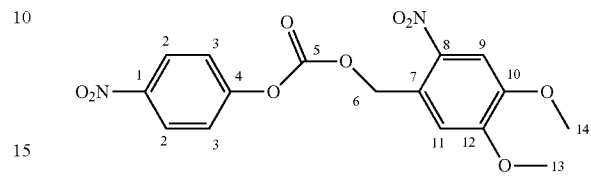

$^1$H-NMR (500 MHZ, DMSO-$d_6$): δ (ppm)=0.93 (s, 3H, $^4$CH$_3$), 3.13 (d, $^3J_{HH}$=6.4 Hz, 2 H, $^5$CH$_2$), 3.87 (s, 3H, O$^{15}$CH$_3$), 3.91 (s, 3H, O$^{16}$CH$_3$), 4.12 (d, $^2J_{HH}$=10.6 Hz, 2 H, $^2$CH$_2$), 4.22 (d, $^2J_{HH}$=10.6 Hz, 2 H, $^2$CH$_2$), 5.35 (s, 2H, $^8$CH$_2$), 7.20 (s, 1H, $^{12}$CH), 7.67 (t, $^3J_{HH}$=6.3 Hz, 1 H, $^6$NH), 7.70 (s, 1H, $^{11}$CH).

$^{13}$C-NMR (125 MHz, DMSO-$d_6$): δ (ppm)=16.70 (1 C, $^4$CH$_3$), 32.70 (1 C, $^3$C$_q$), 43.12 (1 C, $^5$CH$_2$), 56.23 (1 C, O$^{15}$CH$_3$), 56.35 (1 C, O$^{16}$CH$_3$), 62.74 (1 C, $^8$CH$_2$), 73.90 (2 C, $^2$CH$_2$), 108.35 (1 C, $^{11}$CH), 111.01 (1 C, $^{12}$CH), 127.60 (1 C, $^9$C$_q$), 139.60 (1 C, $^{10}$C$_q$), 147.65 (1 C, $^1$C$_q$), 147.95 (1 C, $^{13}$C$_q$), 153.39 (1 C, $^{14}$C$_q$), 156.53 (1 C, $^7$C$_q$).

ESI-ToF-MS (m/z): [M+Na]$^+$ calculated for C$_{16}$H$_{20}$N$_2$O$_9$, 407.1066; found, 407.1067.

Synthesis of 4,5-dimethoxy-2-nitrobenzyl (4-nitrophenyl) carbonate (8)

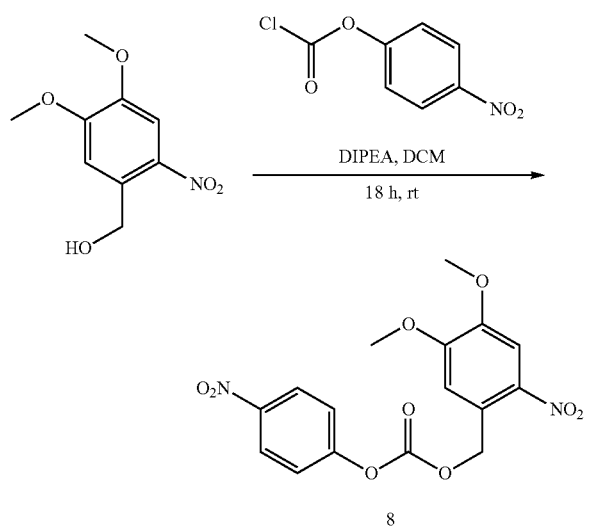

8 was synthesized according to the literature, see N. Fomina, C. McFearin, M. Sermsakdi, O. Edigin and A. Almutairi, UV and Near-IR Triggered Release from Polymeric Nanoparticles, *J. Am. Chem. Soc.,* 2010, 132, 9540-9542.

To a mixture of 8.80 g 4,5-dimethoxy-2-nitrobenzyl alcohol (41.28 mmol), 15.55 g 4-nitrophenyl chloroformate (77.15 mmol), and 90 mL DCM was added dropwise 15 mL diisopropylethylamine (DIPEA) (86.11 mmol) under Ar $^1$H-NMR (500 MHZ, DMSO-$d_6$): δ (ppm)=3.89 (s, 3H, O$^{13}$CH$_3$), 3.92 (s, 3H, O$^{14}$CH$_3$), 5.61 (s, 2H, $^6$CH$_2$), 7.26 (s, 1H, $^{11}$CH), 7.59 (d, $^3J_{HH}$=9.1 Hz, 2 H, $^3$CH), 7.73 (s, 1H, $^9$CH), 8.33 (d, $^3J_{HH}$=9.1 Hz, 2 H, $^2$CH).

$^{13}$C-NMR (125 MHZ, DMSO-$d_6$): δ (ppm)=56.14 (1 C, O$^{13}$CH$_3$), 56.32 (1 C, O$^{14}$CH$_3$), 67.22 (1 C, $^6$CH$_2$), 108.30 (1 C, $^9$CH), 112.00 (1 C, $^{11}$CH), 122.57 (2 C, $^3$CH), 124.37 (1 C, $^7$C$_q$), 125.45 (2 C, $^2$CH), 139.04 (1 C, $^8$C$_q$), 145.25 (1 C, $^1$C$_q$), 148.40 (1 C, $^{12}$C$_q$), 151.62 (1 C, $^5$C$_q$), 153.17 (1 C, $^{10}$C$_q$), 155.17 (1 C, $^4$C$_q$).

Example 1b

Synthesis of light-sensitive polycarbonate (PC01) by ring-opening polymerization of 1,3-dioxan-2-one (TMC) and 4,5-dimethoxy-2-nitrobenzyl ((5-methyl-2-oxo-1,3-dioxan-5-yl)methyl) carbamate (7)

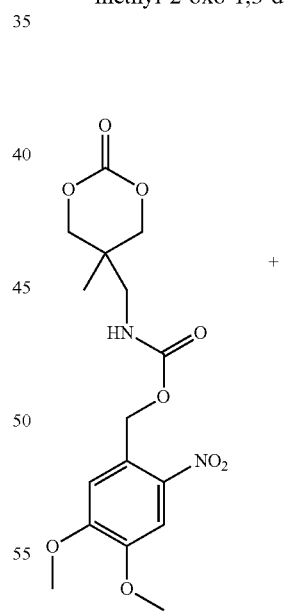

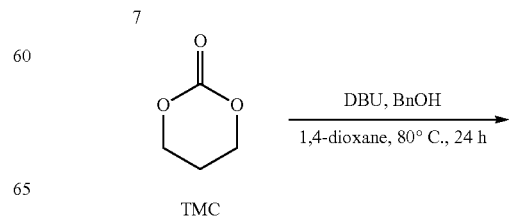

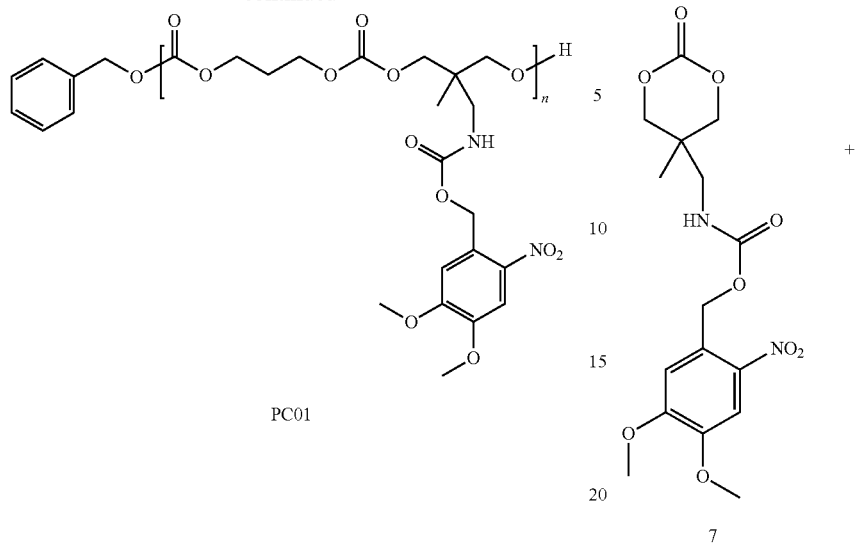

PC01

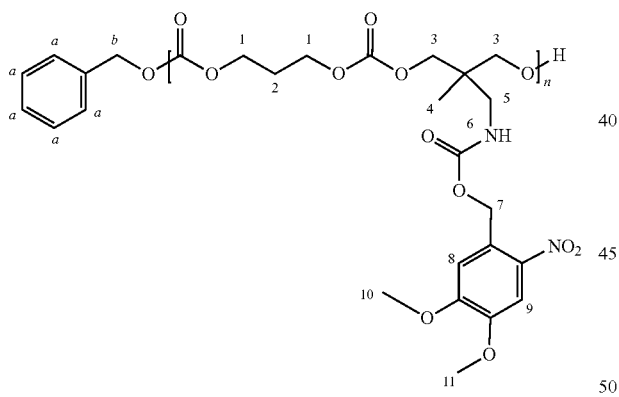

¹H-NMR (500 MHZ, DMSO-d₆): δ (ppm)=0.70-1.00 (m, 3H, $^4CH_3$), 1.80-2.00 (m, 2H, $^2CH_2$), 2.90-3.10 (m, 2H, $^5CH_2$), 3.75-4.00 (m, 3H, $O^{10}CH_3$; 3 H, $O^{11}CH_3$; 4 H, $^3CH_2$), 4.00-4.25 (m, 4H, $^1CH_2$), 5.11 (s, 2H, $^bCH_2$), 5.25-5.40 (m, 2H, $^7CH_2$), 7.00-7.85 (m, 1H, $^6NH$; 2 H, $^{8,9}CH$; 5 H, $^aCH$).

Example 1c

Synthesis of light-sensitive sensitive PEGylated polycarbonate (PC01-PEG) by ring-opening polymerization of 1,3-dioxan-2-one (TMC) and 4,5-dimethoxy-2-nitrobenzyl ((5-methyl-2-oxo-1,3-dioxan-5-yl)methyl) carbamate (7) using poly(ethylene glycol) methyl ether (PEG) as initiator In a Schlenk tube, 0.461 g of 7 (1.20 mmol), 0.123 g TMC (1.20 mmol) and 4.16 μL BnOH (0.04 mmol) were suspended in 2 mL dry 1,4-dioxane under Ar atmosphere. After adding 9.06 μL DBU (0.06 mmol) the reaction mixture was stirred at 80° C. for 24 h and then quenched by adding 10 mg benzoic acid (0.07 mmol). The polymer was purified by precipitation into diethyl ether and dried in vacuo to give a yellow solid. Yield: 73%, $\overline{M}w$=6500 g/mol, $Đ_M$=1.47

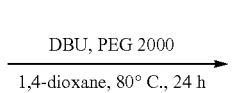

TMC

PC01-PEG

In a Schlenk tube 0.231 g of 7 (0.60 mmol), 0.061 g TMC (0.60 mmol) and 0.040 g PEG 2000 (0.02 mmol) were suspended in 2 mL dry 1,4-dioxane under Ar atmosphere. After adding 4.53 μL DBU (0.03 mmol) the reaction mixture was stirred at 80° C. for 24 h and then quenched by adding 5 mg benzoic acid (0.035 mmol). The polymer was purified by precipitation into diethyl ether and dried in vacuo to give a yellow solid. Yield: 72%, $\overline{M}w$=5000 g/mol, $Đ_M$=1.61

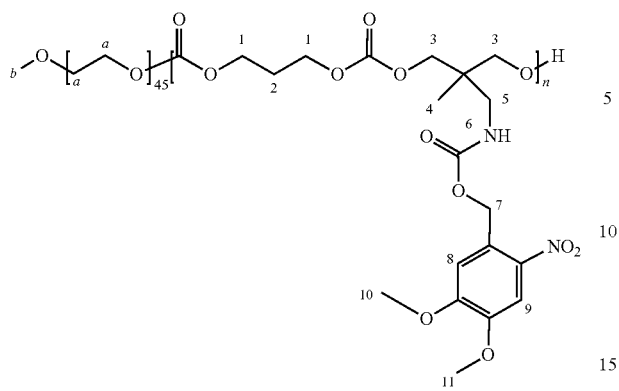

$^1$H-NMR (500 MHz, DMSO-$d_6$): ¿ (ppm)=0.70-1.00 (m, 3H, $^4CH_3$), 1.80-2.00 (m, 2H, $^2CH_2$), 2.90-3.10 (m, 2H, $^5CH_2$), 3.35-3.60 (m, 4H, $^aCH_2$; 3 H, $O^bCH_3$), 3.75-4.00 (m, 3H, $O^{10}CH_3$; 3 H, $O^{11}CH_3$; 4 H, $^3CH_2$), 4.00-4.25 (m, 4H, $^1CH_2$), 5.25-5.40 (m, 2H, $^7CH_2$), 7.00-7.85 (m, 1H, $^6NH$; 2 H, $^{8,9}CH$).

Example 1d

Synthesis of light-sensitive polycarbonate (PC02) by polycondensation of 4,5-dimethoxy-2-nitrobenzyl (3-hydroxy-2-(hydroxymethyl)-2-methylpropyl)-carbamate (6) and a diol with diphenylcarbonate (DPC)

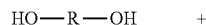

HO—R—OH     +
diol

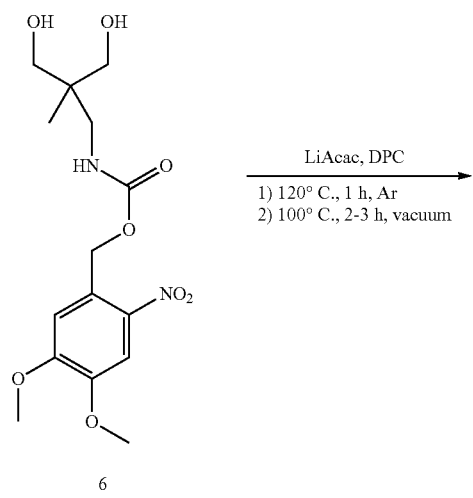

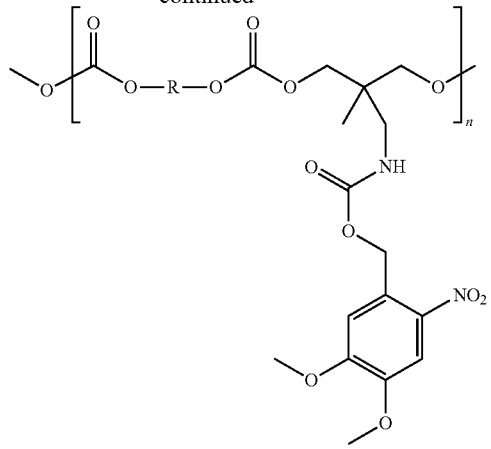

PC02

In a Schlenk flask 0.250 g of 6 (0.698 mmol), diol (0.698 mmol), 0.329 g of DPC (1.536 mmol) and 0.3 mg lithiumacetylacetonate (LiAcac) (0.0028 mmol) were added under Ar atmosphere. The used diols are listed in TABLE 1.

TABLE 1

Results of light degradable PC02 synthesis

| Code | Diols | $\overline{M}_w$ (g/mol) | $Đ_M^1$ | Yields |
|---|---|---|---|---|
| PCO2-BD | 1,4-Butanediol (BD) | 8,100 | 2.02 | 77% |
| PCO2-PD | 1,5-Pentanediol (PD) | 9,300 | 2.27 | 77% |
| PCO2-HD | 1,6-Hexanediol (HD) | 9,500 | 1.86 | 81% |
| PCO2-CDM | 1,4-Cyclohexanedimethanol (CDM) | 6,600 | 1.58 | 70% |
| PCO2-BDM | 1,4-Benzenedimethanol (BDM) | 7,200 | 1.66 | 74% |

[1]Determined using APC in THF/DMF (8/2) with PMMA standards, $\overline{M}_w$, being the molecular weight and $Đ_M^1$ being the polydispersity index, PDI, of the polymer.

The reaction mixture was stirred at 120° C. for 1 h and then at 100° C. for an additional 2 h under reduced pressure. The mixture was then cooled to room temperature and dissolved in DCM. The polymer was purified by precipitation into diethyl ether and dried in vacuo to give a yellow solid. Yield: 70-81%, polymer characteristics were shown in TABLE 1.

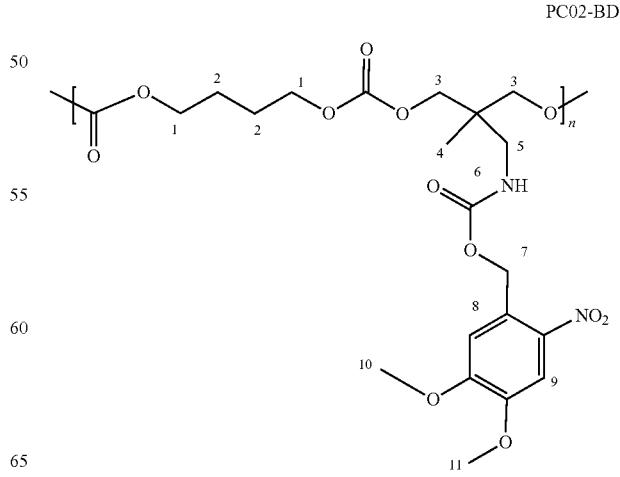

PC02-BD $^1$H-NMR (500 MHz, DMSO-d$_6$): δ (ppm)=0.70-1.00 (m, 3H, $^4$CH$_3$), 1.50-1.80 (m, 4H, $^2$CH$_2$), 2.90-3.10 (m, 2H, $^5$CH$_2$), 3.75-4.00 (m, 3H, O$^{10}$CH$_3$; 3 H, O$^{11}$CH$_3$; 4 H, $^3$CH$_2$), 4.00-4.25 (m, 4H, $^1$CH$_2$), 5.25-5.40 (m, 2H, $^7$CH$_2$), 7.00-7.85 (m, 1H, $^6$NH; 2 H, $^{8,9}$CH).

PC02-PD

[structure diagram]

$^1$H-NMR (500 MHZ, DMSO-d$_6$): δ (ppm)=0.70-1.00 (m, 3H, $^4$CH$_3$), 1.25-1.80 (m, 6H, $^2$CH$_2$), 2.90-3.20 (m, 2H, $^5$CH$_2$), 3.75-4.00 (m, 3H, O$^{10}$CH$_3$; 3 H, O$^{11}$CH$_3$; 4 H, $^3$CH$_2$), 4.00-4.25 (m, 4H, $^1$CH$_2$), 5.25-5.40 (m, 2H, $^7$CH$_2$), 7.00-7.80 (m, 1H, $^6$NH; 2 H, $^{8,9}$CH).

PC02-HD

[structure diagram]

$^1$H-NMR (500 MHz, DMSO-d$_6$): δ (ppm)=0.70-1.00 (m, 3H, $^4$CH$_3$), 1.25-1.80 (m, 8H, $^2$CH$_2$), 2.90-3.20 (m, 2H, $^5$CH$_2$), 3.75-4.00 (m, 3H, O$^{10}$CH$_3$; 3 H, O$^{11}$CH$_3$; 4 H, $^3$CH$_2$), 4.00-4.25 (m, 4H, $^1$CH$_2$), 5.25-5.40 (m, 2H, $^7$CH$_2$), 7.00-7.80 (m, 1H, $^6$NH; 2 H, $^{8,9}$CH).

PC02-CDM

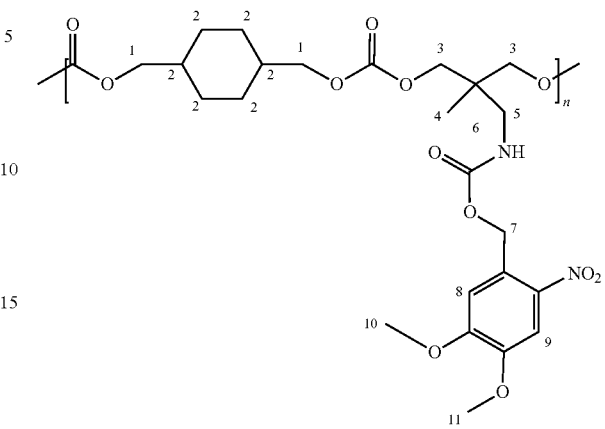

$^1$H-NMR (500 MHz, DMSO-d$_6$): δ (ppm)=0.75-1.85 (m, 3H, $^4$CH$_3$; 10 H, $^2$CH$_2$), 2.90-3.20 (m, 2H, $^5$CH$_2$), 3.70-4.20 (m, 3H, O$^{10}$CH$_3$; 3 H, O$^{11}$CH$_3$; 4 H, $^3$CH$_2$; 4 H, $^1$CH$_2$), 5.25-5.40 (m, 2H, $^7$CH$_2$), 7.00-7.80 (m, 1H, $^6$NH; 2 H, $^{8,9}$CH).

PC02-BDM

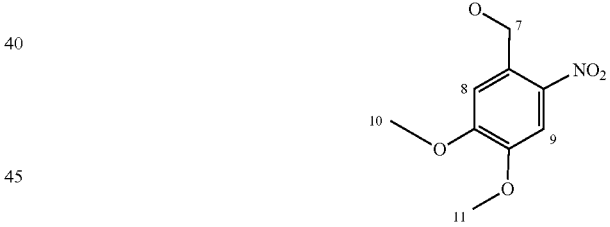

$^1$H-NMR (500 MHZ, DMSO-d$_6$): δ (ppm)=0.70-1.00 (m, 3H, $^4$CH$_3$), 2.90-3.20 (m, 2H, $^5$CH$_2$), 3.75-4.10 (m, 3H, O$^{10}$CH$_3$; 3 H, O$^{11}$CH$_3$; 4 H, $^3$CH$_2$), 4.90-5.25 (m, 4H, $^1$CH$_2$), 5.25-5.50 (m, 2H, $^7$CH$_2$), 7.00-7.80 (m, 4H, $^2$CH; 1 H, $^6$NH; 2 H, $^{8,9}$CH).

Example 1e

Synthesis of 4,5-dimethoxy-2-nitrobenzyl (1,3-dihydroxypropan-2-yl) carbamate (9)

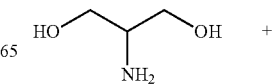 +

-continued

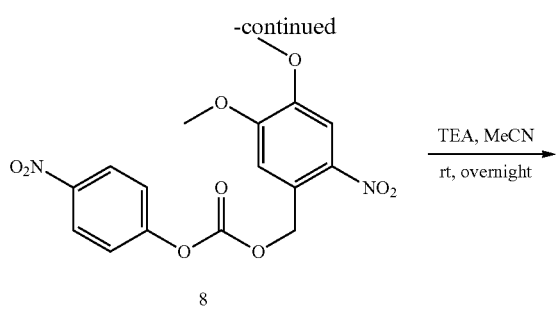

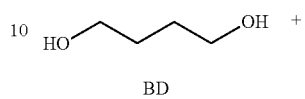

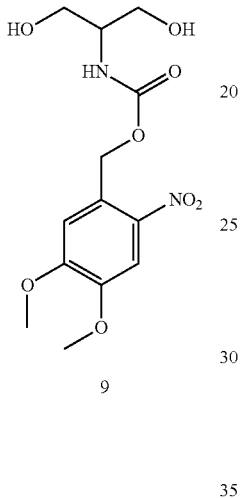

9

In a round bottom flask 2.94 g serinol (27.75 mmol), 7.00 g of 8 (18.50 mmol), 9.66 mL TEA (69.38 mmol) were suspended in 140 mL dry MeCN. The reaction mixture was stirred at room temperature overnight. The precipitate was collected by filtration, washed with 150 mL DCM and dried in vacuo to achieve 3.97 g of an off-white solid. Yield: 65%

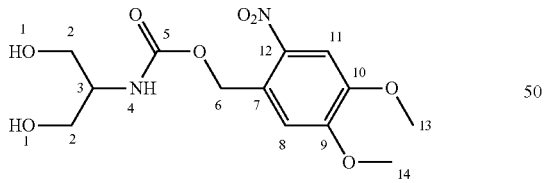

$^1$H-NMR (500 MHZ, DMSO-d$_6$): δ (ppm)=3.30-3.60 (m, 4H, $^2$CH$_2$; 1 H, $^3$CH), 3.87 (s, 3H, O$^{14}$CH$_3$), 3.91 (s, 3H, O$^{13}$CH$_3$), 4.59 (t, $^3$J$_{HH}$=5.4 Hz, 2 H, $^1$OH), 5.33 (s, 2H, $^6$CH$_2$), 7.14 (d, $^3$J$_{HH}$=8.0 Hz, 1H, $^4$NH), 7.21 (s, 1H, $^8$CH), 7.69 (s, 1H, $^{11}$CH).

$^{13}$C-NMR (125 MHz, DMSO-d$_6$): δ (ppm)=55.49 (1 C, $^3$CH), 56.55 (1 C, O$^{14}$CH$_3$), 56.73 (1 C, O$^{13}$CH$_3$), 60.96 (2 C, $^2$CH$_2$), 62.69 (1 C, $^6$CH$_2$), 108.58 (1 C, $^{11}$CH), 110.73 (1 C, $^8$CH), 128.76 (1 C, $^7$C$_q$), 139.53 (1 C, $^{12}$C$_q$), 148.09 (1 C, $^9$C$_q$), 153.96 (1 C, $^{10}$C$_q$), 156.00 (1 C, $^5$C$_q$). ESI-ToF-MS (m/z): [M+Na]$^+$ calculated for C$_{13}$H$_{18}$N$_2$O$_8$, 353.0961; found, 353.0959.

Example 1f

Synthesis of light-sensitive polycarbonate (PC03) by polycondensation of 4,5-dimethoxy-2-nitrobenzyl (1,3-dihydroxypropan-2-yl) carbamate (9) and 1,4-butanediol (BD) with triphosgene

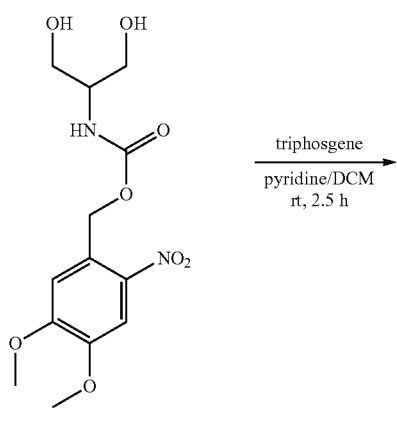

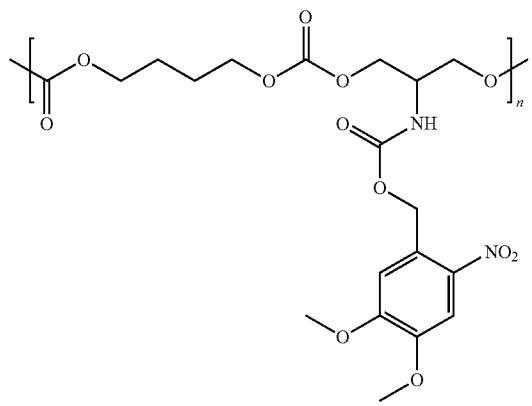

PC03

In a Schlenk flask 0.180 g triphosgene (0.607 mmol) was dissolved in 0.6 mL DCM under Ar atmosphere. A solution of 0.300 g of 9 (0.909 mmol) and 0.086 g BD (0.909 mmol) in 0.9 mL pyridine (11 mmol) was added dropwise over 90 min. After complete addition, the mixture was allowed to stir for an additional 1 h. The DCM was removed under reduced pressure. The polymer was purified by precipitation into water/MeOH (v/v=1/1) mixture and dried in vacuo to give a yellow solid. Yield: 63%, $\overline{M}w$=5300 g/mol, $Đ_M$=1.57

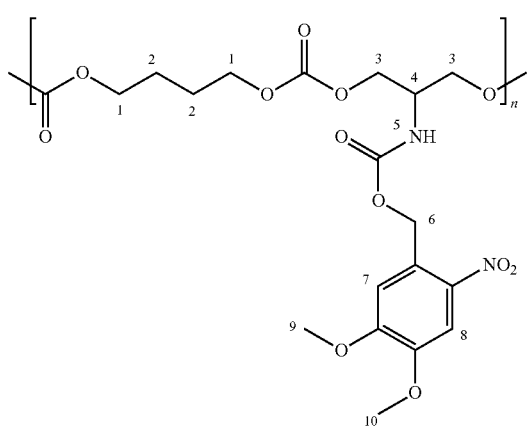

$^1$H-NMR (500 MHZ, DMSO-d$_6$): δ (ppm)=1.50-1.80 (m, 4H, $^2$CH$_2$), 3.50-4.30 (m, 4H, $^1$CH$_2$; 4 H, $^3$CH$_2$; 1 H, 4CH; 3 H, O$^9$CH$_3$; 3 H, O$^{10}$CH$_3$), 5.20-5.40 (m, 2H, $^6$CH$_2$), 7.00-7.25 (m, 1H, $^7$CH), 7.50-7.90 (m, 1H, $^5$NH; 1 H, $^8$CH).

Example 1g

Synthesis of light-sensitive polyester (PE) by polycondensation of 4,5-dimethoxy-2-nitrobenzyl (1,3-dihydroxypropan-2-yl) carbamate (9) with adipoyl chloride (AC)

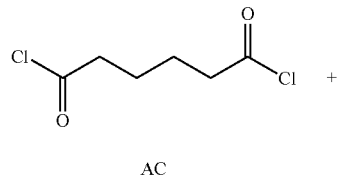

AC

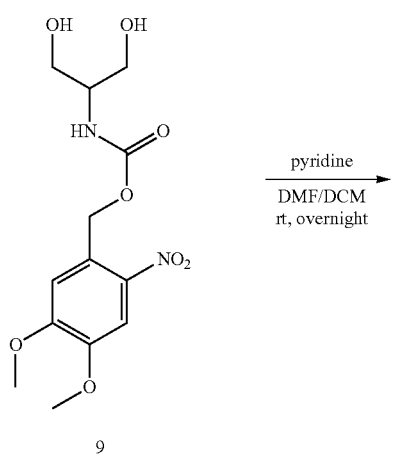

9

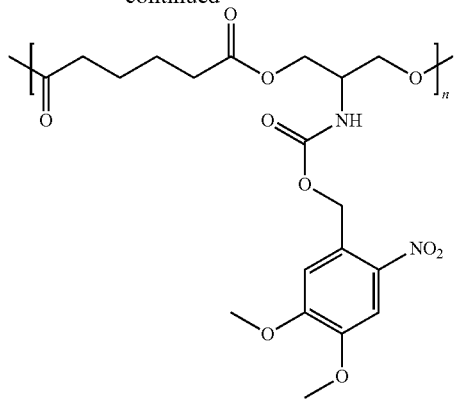

PE

In a Schlenk flask 0.330 g of 9 (1.0 mmol), 0.18 mL pyridine (2.2 mmol) was dissolved in 5 mL DMF under Ar atmosphere. A solution of 0.192 g AC (1.05 mmol) in 2 mL DCM was added dropwise over 30 min. After complete addition, the mixture was allowed to stir overnight. The DCM was removed under reduced pressure. The polymer was purified by precipitation into water/MeOH (v/v=1/1) mixture and dried in vacuo to give a yellow solid. Yield: 80%, $\overline{M}w$=3300 g/mol, $Đ_M$=1.55

$^1$H-NMR (500 MHZ, DMSO-d$_6$): δ (ppm)=1.40-1.80 (m, 4H, $^2$CH$_2$), 2.15-2.35 (m, 4H, $^1$CH$_2$), 3.75-3.95 (m, 3H, O$^9$CH$_3$; 3 H, O$^{10}$CH$_3$), 3.95-4.30 (m, 4H, $^3$CH$_2$; 1 H, $^4$CH), 5.25-5.40 (m, 2H, $^6$CH$_2$), 7.10-7.25 (m, 1H, $^7$CH), 7.55-7.80 (m, 1H, $^5$NH; 1 H, $^8$CH).

Example 1h

Light Degradation Investigation of PC01 with 1H NMR Spectroscopy

PC01 solution was prepared in a vial at 15 mg/mL in DMSO-d$_6$. The PC01 solution was irradiated directly in vial with UV light (0.607 W/cm$^2$) for 15 min and 1H NMR spectrum was taken. The 1H NMR spectra of PC01 before and after light degradation are shown in FIG. 1 and the signal of $^2$CH$_3$ was used as reference, because the relative integral of $^2$CH$_3$ should remain unchanged. The result from 1H NMR spectroscopy before irradiation (FIG. 1a) conformed fully to polymer structure as expected. Upon irradiation for 15 min (FIG. 1b) the relative integral of characteristic NMR peak corresponding to the 3CH$_2$ reduced from 1.69 to 0.13 indicating about 92% cleavage of the light-sensitive 4,5-dimethoxy-2-nitrobenzyl group. As a result of the subsequent intramolecular cyclization the peak at 3.94 ppm for polymer backbone ($^1$CH$_2$) reduced significantly and changed from broad peak to sharper small molecule peaks. The newly generated degradation products were observed between 3.50 and 3.80 ppm as well.

Example 1i

Light Degradation Investigation of PC01 with APC

Figure 2:
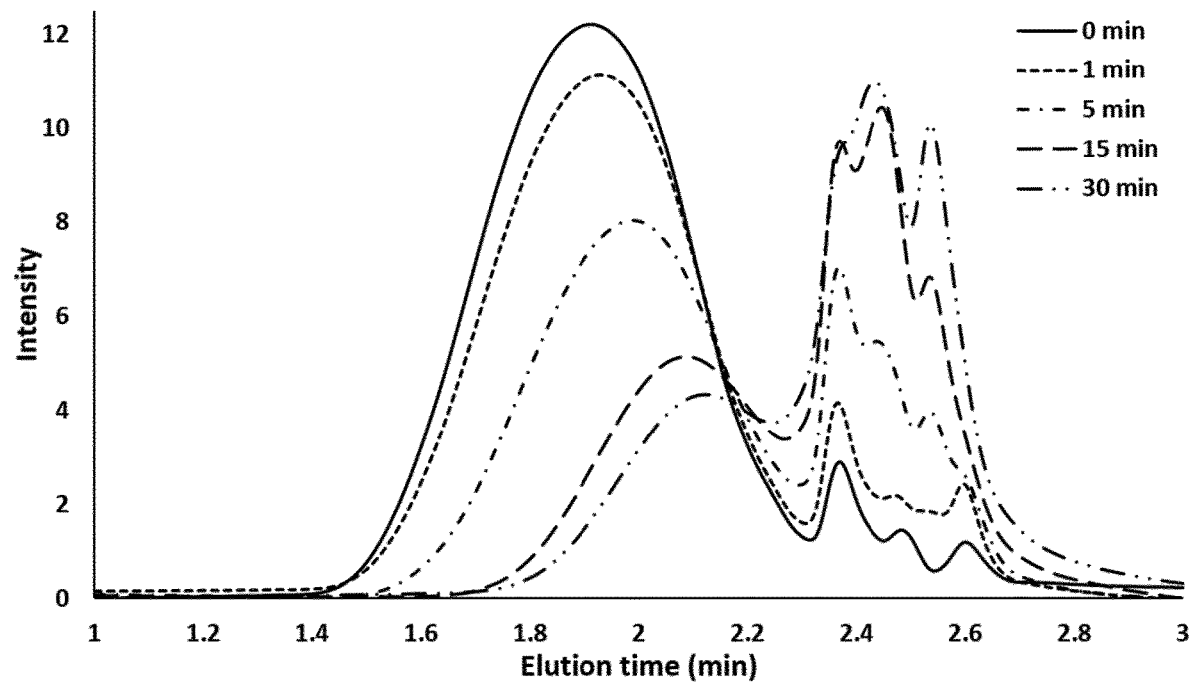
FIG. 2 shows APC traces of PC01 in THE after irradiation with UV light (320-480 nm, 0.603 W/cm$^2$) for 0, 1, 5, 15 and 30 min.

Five polymer solutions of PC01 were prepared in APC vials at 2 mg/mL in THF. These samples were irradiated by UV light (0.607 W/cm$^2$, 320-410 nm) for the specified times of 0, 1, 5, 15 and 30 min, and the molar masses were investigated by APC. FIG. 2 shows the APC traces of PC01 before and after light degradation. The degradation degree of PC was strongly affected by irradiation times. With increasing irradiation times, the peak maxima of APC traces for polymers shifted to low molar mass regions due to the loss of light sensitive protecting groups and subsequent polymer degradation caused by intramolecular cyclization, while more and more small molecules were observed in low molar mass region. More importantly, the polymer peak area, which is proportional to the number of polymer chains, consistently decreased upon irradiation, indicating strongly that the polymer chains were fragmented as a result of intramolecular cyclization. The small difference in APC traces for 15 and 30 min suggested that the rapid degradation process completed within 15 min of irradiation.

Example 1j

Light Degradation Investigation of PC01 with UV-VIS Spectrophotometer

Figure 3:
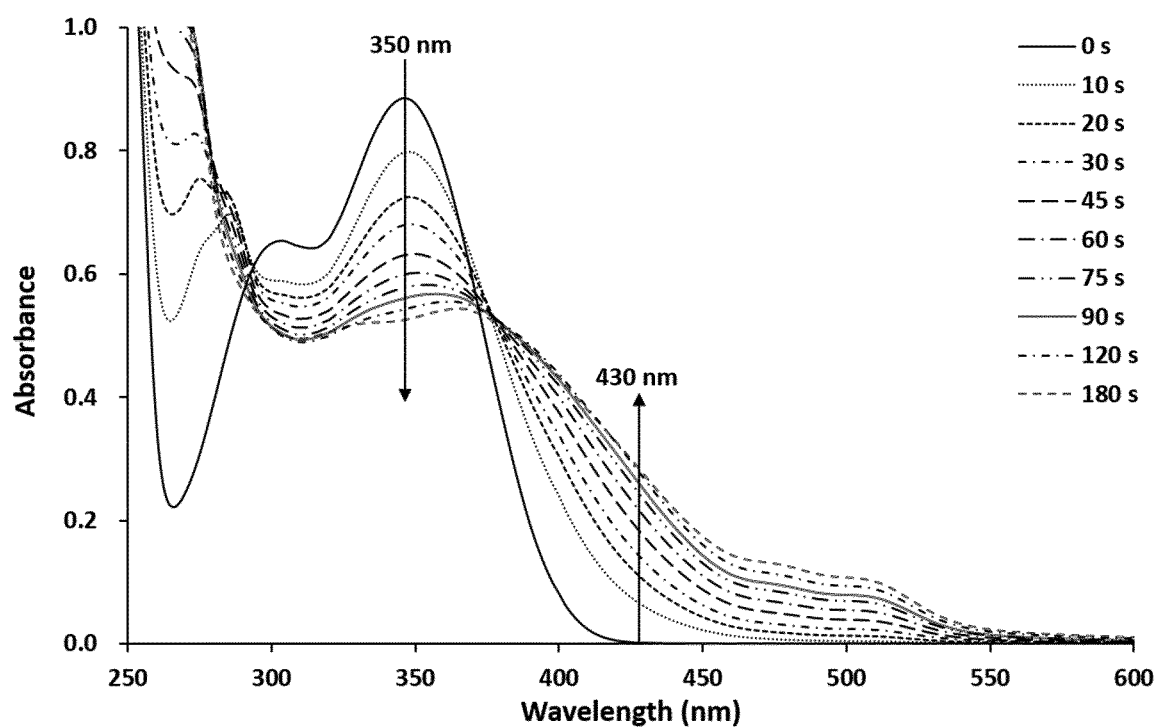
FIG. 3 shows UV-VIS spectra of PC01 in DCM after irradiation with UV light (320-480 nm, 0.603 W/cm$^2$) for 0, 10, 20, 30, 45, 60, 75, 90, 120 and 180 s.

A polymer solution of PC01 was prepared at 0.075 mg/mL in DCM. The PC01 solution was irradiated in quartz cuvette with UV light (0.607 W/cm$^2$) for the specified periods of time up to 180 s (FIG. 3). UV-VIS absorbance spectra were recorded after each irradiation. Upon irradiation the absorbance at 346 nm decreased due to the cleavage of 4,5-dimethoxy-2-nitrobenzyl light-sensitive protecting group, while a new absorbance appeared at 430 nm, which could be assigned to the degradation product of 4,5-dimethoxy-2-nitrobenzaldehyde. The UV-VIS spectrum remained unchanged after irradiation for 180 s indicating complete cleavage of protecting group from polymer side chains.

Example 2a

Preparation and Characterization of Light-Cleavable Nanoparticles (NP) Based on Polycarbonate (PC) and Poly(DL-Lactide-Co-Glycolide) (PLGA) with the Photosensitizer (PS) 5,10,15,20-Tetrakis(3-Hydroxyphenyl)-Chlorin (mTHPC) in a Size Range of about 100 nm
(Further Abbreviated as mTHPC—PC-PLGA-NP100)

The light-cleavable composition was prepared by a solvent displacement preparation technique. In brief, 7.5 mg light-cleavable polymer (PC) and 22.5 mg of the FDA-approved polymer PLGA were dissolved in 1 mL acetone, respectively. After combining both organic solutions, 3 mg of the PS mTHPC was added and dissolved. The organic solution was injected into 4 mL of an aqueous PVA solution (2% (w/v)). The nanoparticle suspension was stirred overnight, whereby evaporation of the organic solvent led to the final particle formation. Afterwards, purification of the nanoparticle suspension was conducted three times via centrifugation (30,000 g, 1.5 h) and redispersion in water. To obtain unloaded nanoparticles the preparation process was performed in the absence of PS.

For physicochemical particle characterization, photon correlation spectroscopy (PCS) measurements of diluted nanoparticle suspensions were performed. Therefore, a Malvern Zetasizer Nano ZS system was used (Malvern Instruments Ltd., Malvern, UK). The hydrodynamic diameter and polydispersity index (PDI) were measured at a temperature of 22° C. and a backscatter angle of 173°. The surface charge of the nanoparticles was determined by laser Doppler microelectrophoresis using the zeta potential mode.

The amount of the incorporated PS (mTHPC) was determined by HPLC. The nanoparticles were dissolved in acetone and subsequently, the dissolved PS was quantified via high performance liquid chromatography (HPLC) with the aid of a calibration curve of pure mTHPC (concentration range from 10 to 100 µg/mL). An HPLC-DAD system (Agilent Technologies 1200 series) with a reversed phase column (Gemini RP 18; 250×4.6 mm, particle diameter 5 µm (Phenomenex, Aschaffenburg, Germany)) was used. The mobile phase consisting of 42.5% water with 0.1% (w/v) trifluoroacetic acid and 57.5% acetonitrile was isocratic eluted at a flow rate of 1.0 mL/min. The PS was detected at a wavelength of 415 nm. TABLE 2 shows the obtained nanoparticle characteristics.

TABLE 2 shows the physicochemical characteristics of unloaded and mTHPC-loaded light-cleavable nanoparticles (mean ± S.D.; n = 3) prepared using the described Examples 2a-d.

| Ex. | Nanoparticle system | Hydrodynamic diameter (nm) | PDI | Zetapotential (mV) | Drug load (µg mTHPC/ mg NP) |
|---|---|---|---|---|---|
| 2a | PC-PLGA-NP100 | 116.0 | 0.10 | −22.0 | — |
|  | mTHPC-PC-PLGA-NP100 | 109.3 ± 4.1 | 0.08 ± 0.01 | −29.2 ± 1.2 | 67.4 ± 13.7 |
|  | PC-(PLA-PEG)-PLGA-NP100 | 84.8 ± 3.2 | 0.16 ± 0.04 | −16.8 ± 3.0 | — |
| 2b | mTHPC-PC-(PLA-PEG)-PLGA-NP100 | 98.3 ± 7.7 | 0.09 ± 0.01 | −18.9 ± 2.7 | 96.1 ± 13.7 |
|  | (PC-PEG)-PLGA-NP100 | 104.9 | 0.10 | −22.9 | — |
| 2c | mTHPC-(PC-PEG)-PLGA-NP100 | 103.4 ± 10.8 | 0.09 ± 0.02 | −24.5 ± 4.3 | 94.5 ± 10.1 |
| 2d | PC-PLGA-NP200 | 231.4 ± 10.0 | 0.06 ± 0.04 | −25.3 ± 0.4 | — |
|  | mTHPC-PC-PLGA-NP200 | 229.2 | 0.09 | −26.9 | 121.2 |

Investigation of Light-Induced Nanoparticle Degradation

Figure 4:
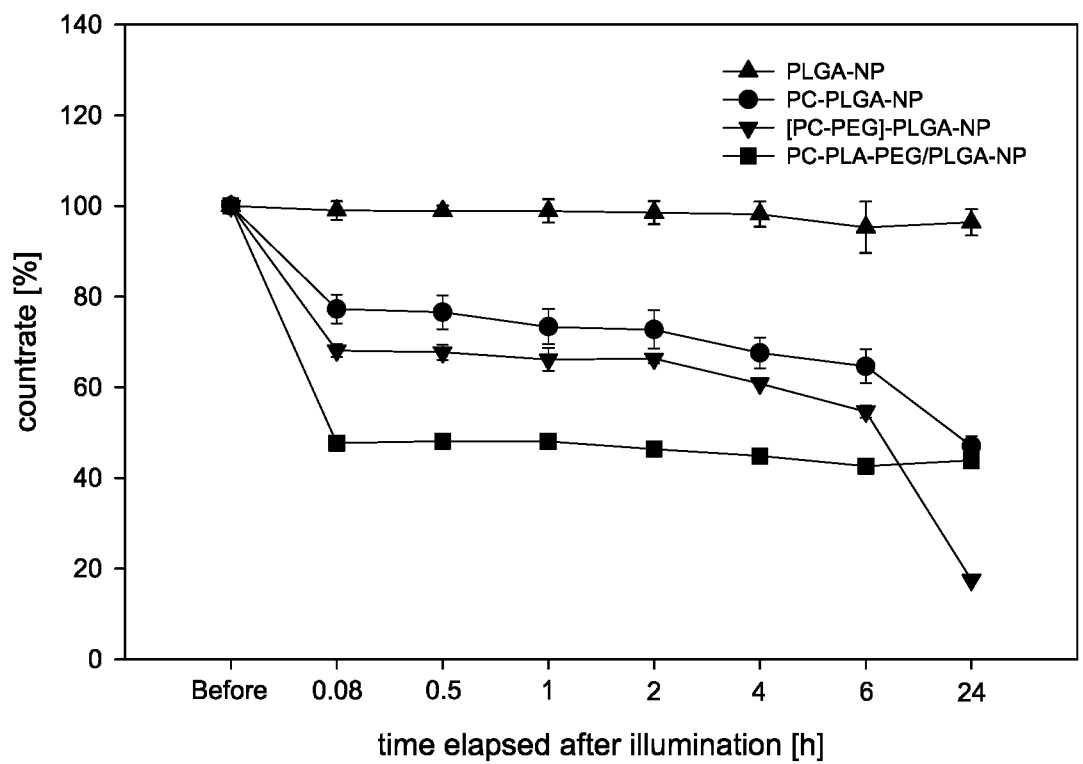
FIG. 4 shows the light-induced desintegration of nanoparticles measured by variation of the PCS count rate (mean±S.D.; n=3) of different nanoparticle suspensions over 24 h after irradiation with light of a wavelength of 365 nm for 5 min.

Light-depending particle degradation was investigated after irradiation of a diluted nanoparticle suspension (0.1 mg NP/mL suspension) with light of a wavelength of 365 nm for 5 min. Variations in the count rate of the nanoparticle suspensions were observed over 24 h via PCS measurements at a temperature of 22° C. and a backscatter angle of 173°. FIG. 4 shows the light-induced particle degradation in comparison to other compositions. As illustrated, the tested formulations retained degradation properties after irradiation of the particle suspensions for 5 min, reflected by a decrease of the particle count rate. In contrast, standard PLGA-NP without a light-cleavable polymer showed no light-depending degradation.

Analysis of the Light-Dependent Drug Release Kinetics

Figure 5:
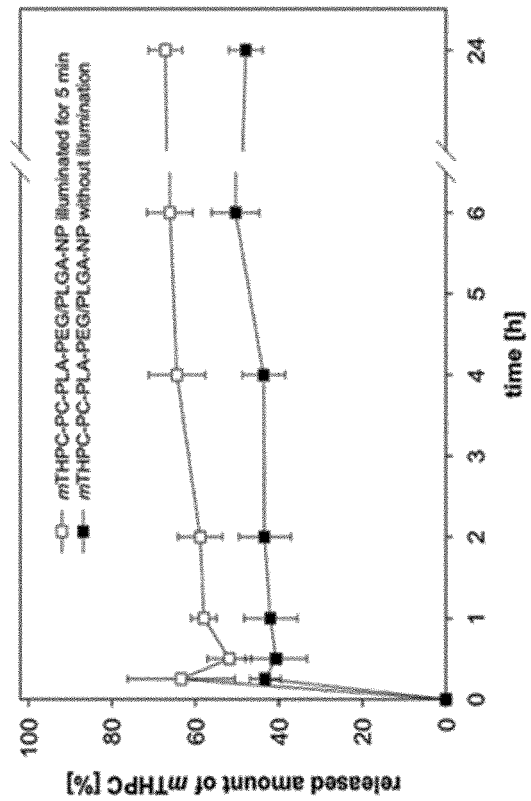
FIG. 5 depicts the amount of the released photosensitizer mTHPC in dependence of particle light irradiation of mTHPC-PC-PLGA-NP100 (A), mTHPC-PC-(PLA-PEG)-PLGA-NP100 (B), and mTHPC-(PC-PEG)-PLGA-NP100 (C) over 24 h, and the release of the irradiated nanoparticles compared to each other and the non-light-cleavable control mTHPC-PLGA-NP100 (D)
Figure 5:
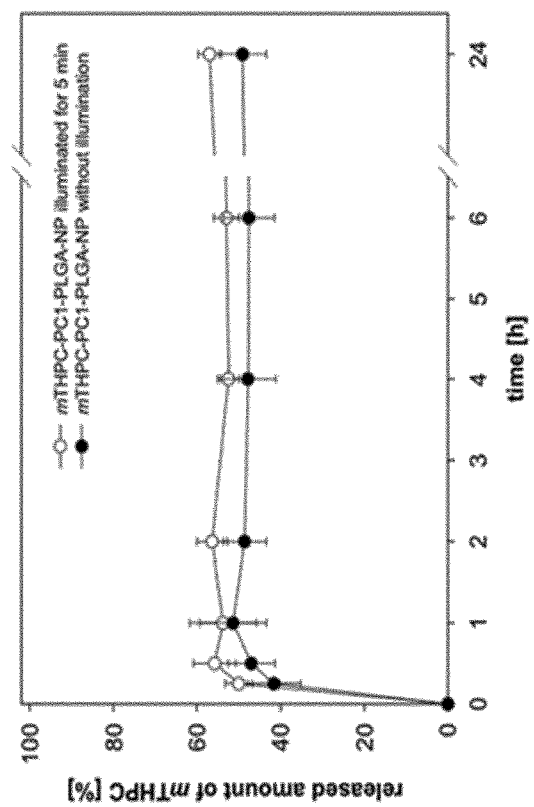
Figure 5:
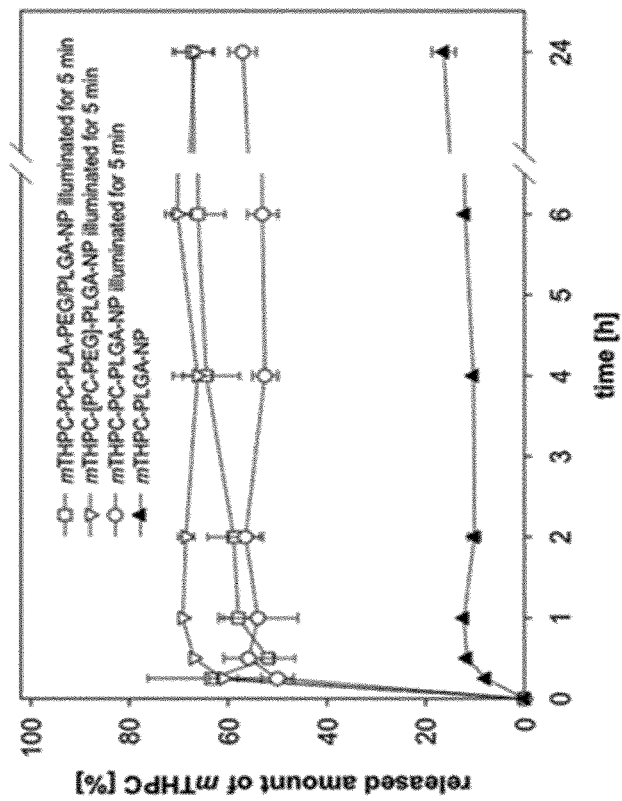
Figure 5:
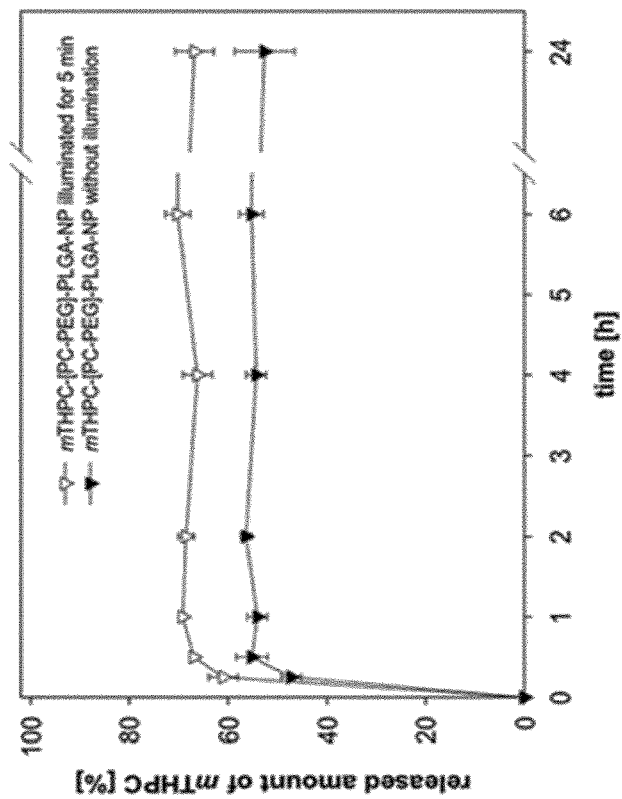

Lyophilized nanoparticles were dispersed in Dulbecco's Modified Eagle Medium (DMEM) containing 10% (v/v) fetal bovine serum (FBS). Afterwards, aliquots of 1 mL were irradiated for 5 min with light of a wavelength of 365 nm and afterwards incubated at 37° C. for defined times (15 min, 30 min, 60 min, 2 h, 4 h, 6 h, 24 h). The collected samples were centrifuged (20,000 g, 15 min) and the supernatants were collected. 150 µL of each supernatant was mixed with 450 µL of acetone to precipitate remaining serum protein and to dissolve the drug. In a further centrifugation step (20,000 g, 10 min), the precipitated proteins were separated and the PS content of the supernatants was determined via HPLC-FLD analysis. The HPLC-parameters were the same as described above, except that released mTHPC was detected with a fluorescence detector at 421 nm excitation and 653 nm emission wavelength. For the non-irradiated control, the experimental setup was performed as described above, except the irradiation for 5 min. The conducted in vitro release studies confirmed the hypothesis, that irradiation of the manufactured systems leads to increased drug release (FIG. 5). Non-irradiated nanoparticles showed lower mTHPC release than irradiated particles. In contrast, nanoparticles including no light-cleavable polymer showed a significant reduced release of the incorporated PS (FIG. 5D).

Example 2b

Preparation and Characterization of Light-Cleavable PEGylated Nanoparticles (NP) Based on Polycarbonate (PC), Poly(Ethylene Glycol) Methyl Ether-Block-Poly(Lactic Acid) (PLA-PEG)-, and Poly(DL-Lactide-Co-Glycolide) (PLGA) with the Photosensitizer (PS) 5,10,15,20-Tetrakis (3-Hydroxyphenyl)-Chlorin (mTHPC) in a Size Range of about 100 nm
(Further Abbreviated as mTHPC-PC-(PLA-PEG)-PLGA-NP100)

To obtain PEGylated light-cleavable nanoparticles 7.5 mg of a polycarbonate-based light-cleavable polymer (PC) was dissolved in 1 mL acetone. A second organic solution was prepared by dissolving 13.5 mg PLA-PEG and 9 mg PLGA in 1 mL acetone. Both organic solutions were combined and 3 mg of the model PS mTHPC were added and dissolved. The organic solution was injected into 4 mL of an aqueous PVA solution (2% (w/v)). The nanoparticle suspension was stirred overnight, whereby evaporation of the organic solvent led to the final particle formation. Afterwards, purification of the nanoparticle suspension was conducted three times via centrifugation (30,000 g, 1.5 h) and redispersion in water. To obtain unloaded nanoparticles the preparation process was performed in the absence of PS. The nanoparticles were characterized as described within Example 2a. TABLE 2 shows the obtained nanoparticle characteristics.

Example 2c

Preparation and Characterization of Light-Cleavable PEGylated Nanoparticles (NP) Based on Polycarbonate-PEG (PC-PEG) and Poly (DL-Lactide-Co-Glycolide) (PLGA) with the Photosensitizer (PS) 5,10,15,20-Tetrakis(3-Hydroxyphenyl)-Chlorin (mTHPC) in a Size Range of about 100 nm
(Further Abbreviated as mTHPC-(PC-PEG)-PLGA-NP100)

For the preparation of PEGylated light-cleavable nanoparticles, 10.7 mg PC-PEG and 19.3 mg PLGA were dissolved in 1 mL acetone, respectively. Afterwards, both organic solutions were combined and 3.0 mg PS (mTHPC) was added and dissolved. The organic solution was injected into 4 mL of an aqueous PVA solution (2% (w/v)). The nanoparticle suspension was stirred overnight, whereby evaporation of the organic solvent led to the final particle formation. Afterwards, purification of the nanoparticle suspension was conducted three times via centrifugation (30,000 g, 1.5 h) and redispersion in water. To obtain unloaded nanoparticles the preparation process was performed in the absence of PS. The nanoparticles were characterized as described within Example 2a. TABLE 2 shows the obtained nanoparticle characteristics.

Example 2d

Preparation and Characterization of Light-Cleavable Nanoparticles (NP) Based on Polycarbonate (PC) and Poly (DL-Lactide-Co-Glycolide) (PLGA) with the Photosensitizer (PS) 5,10,15,20-Tetrakis (3-Hydroxyphenyl)-Chlorin (mTHPC) in a Size Range of about 200 nm
(Further Abbreviated as mTHPC—PC-PLGA-NP200)

For the preparation of nanoparticles in a size range of about 200 nm, an emulsion diffusion method was used. Briefly, 5 mg of the light-cleavable polymer (PC) and 15 mg PLGA were dissolved in a mixture of 1 mL dichloromethane and 1 mL ethyl acetate. Afterwards, 3 mg of the model PS mTHPC was added and dissolved. The organic solution and 2 mL of an aqueous PVA solution (1% (w/v)) were emulsified using an Ultra-Turrax® at 24,000 rpm for 30 min. Afterwards, the pre-emulsion was poured into 8 mL of an aqueous PVA solution (1% (w/v)). The organic solvents were evaporated over night by stirring at 500 rpm. The manufactured nanoparticles were purified in three centrifugation steps (30,000 g, 1 h) with subsequent resuspension in ultrapure water. To obtain unloaded nanoparticles the preparation process was performed in the absence of PS. The nanoparticles were characterized as described within Example 2a. TABLE 2 shows the obtained nanoparticle characteristics.

Example 2e

Preparation and Characterization of Light-Cleavable PEGylated Nanoparticles (NP) with Increased Amounts of Light-Cleavable Polymer Based on Polycarbonate-PEG (PC-PEG) and Poly (DL-Lactide-Co-Glycolide) (PLGA) with the Photosensitizer (PS) 5,10,15,20-Tetrakis (3-Hydroxyphenyl)-Chlorin (mTHPC) in a Size Range of about 100 nm
(Further Abbreviated as mTHPC-(PC-PEG)$_{50\%}$-PLGA$_{50\%}$-NP100 and mTHPC-(PC-PEG)$_{100\%}$-NP100)

For the preparation of PEGylated light-cleavable nanoparticles with increased (50% and 100%) amounts of light-cleavable polymer, 21 mg PC-PEG and 9 mg PLGA (for mTHPC-(PC-PEG)$_{50\%}$-PLGA$_{50\%}$-NP100) or 30 mg (for mTHPC-(PC-PEG)$_{100\%}$-NP100) were dissolved in 2 mL acetone. Afterwards 3.0 mg PS (mTHPC) was added and dissolved. The organic solution was injected into 4 mL of an aqueous PVA solution (2% (w/v)). The nanoparticle suspension was stirred overnight, whereby evaporation of the organic solvent led to the final particle formation. Afterwards, purification of the nanoparticle suspension was conducted three times via centrifugation (30,000 g, 1.5 h) and redispersion in water. The nanoparticles were characterized as described within Example 2a. TABLE 3 shows the obtained nanoparticle characteristics.

TABLE 3 shows the physicochemical characteristics of mTHPC-loaded light-cleavable nanoparticles (mean ± S.D.; n = 3) prepared using the described Examples 2e.

| Nanoparticle system | Hydrodynamic diameter (nm) | PDI | Zetapotential (mV) | Drug load (μg mTHPC/ mg NP) |
|---|---|---|---|---|
| mTHPC-(PC-PEG)-PLGA-NP100 (Example 2c, 25% PC-PEG) | 103.4 ± 10.8 | 0.09 ± 0.02 | −24.5 ± 4.3 | 94.5 ± 10.1 |
| mTHPC-(PC-PEG)$_{50\%}$-PLGA$_{50\%}$-NP100 | 93.0 ± 18.3 | 0.10 ± 0.03 | −20.2 ± 11.9 | 123.7 ± 4.6 |
| mTHPC-(PC-PEG)$_{100\%}$-NP100 | 95.1 ± 4.6 | 0.10 ± 0.03 | −0.2 ± 3.6 | 74.8 ± 2.5 |

Investigation of Light-Induced Nanoparticle Degradation

Figure 6:
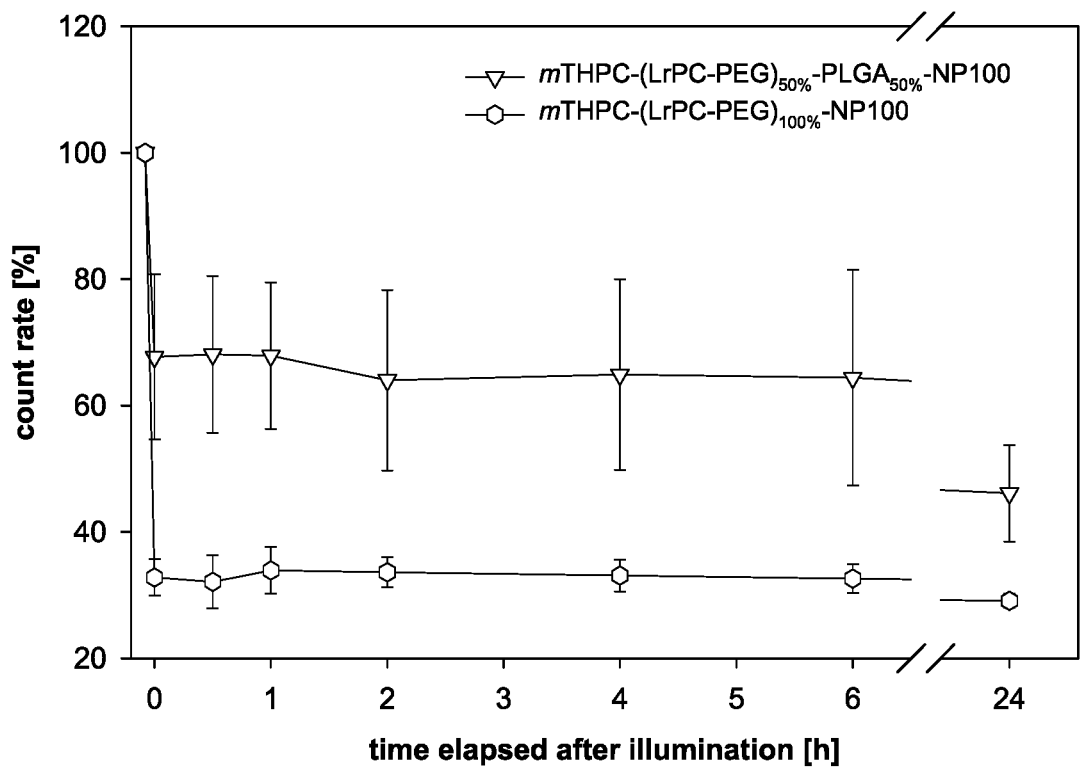
FIG. 6 shows the light-induced variation of the count rate (mean±S.D.; n=3) of different nanoparticle suspensions over 24 h after irradiation with light of a wavelength of 365 nm for 5 min.

FIG. 6 shows the light-induced particle degradation of nanoparticles with 50% and 100% light-responsive polymer. As illustrated, the tested formulations retained degradation properties after irradiation of the particle suspensions for 5 min, reflected by a decrease of the particle count rate. In comparison to nanoparticles with 50% (PC-PEG), nanoparticles with 100% (PC-PEG) showed increased light-induced nanoparticle degradation, due to the increased number of light-responsive groups in the particle matrix.

Analysis of the Light-Dependent Drug Release Kinetics

Figure 7:
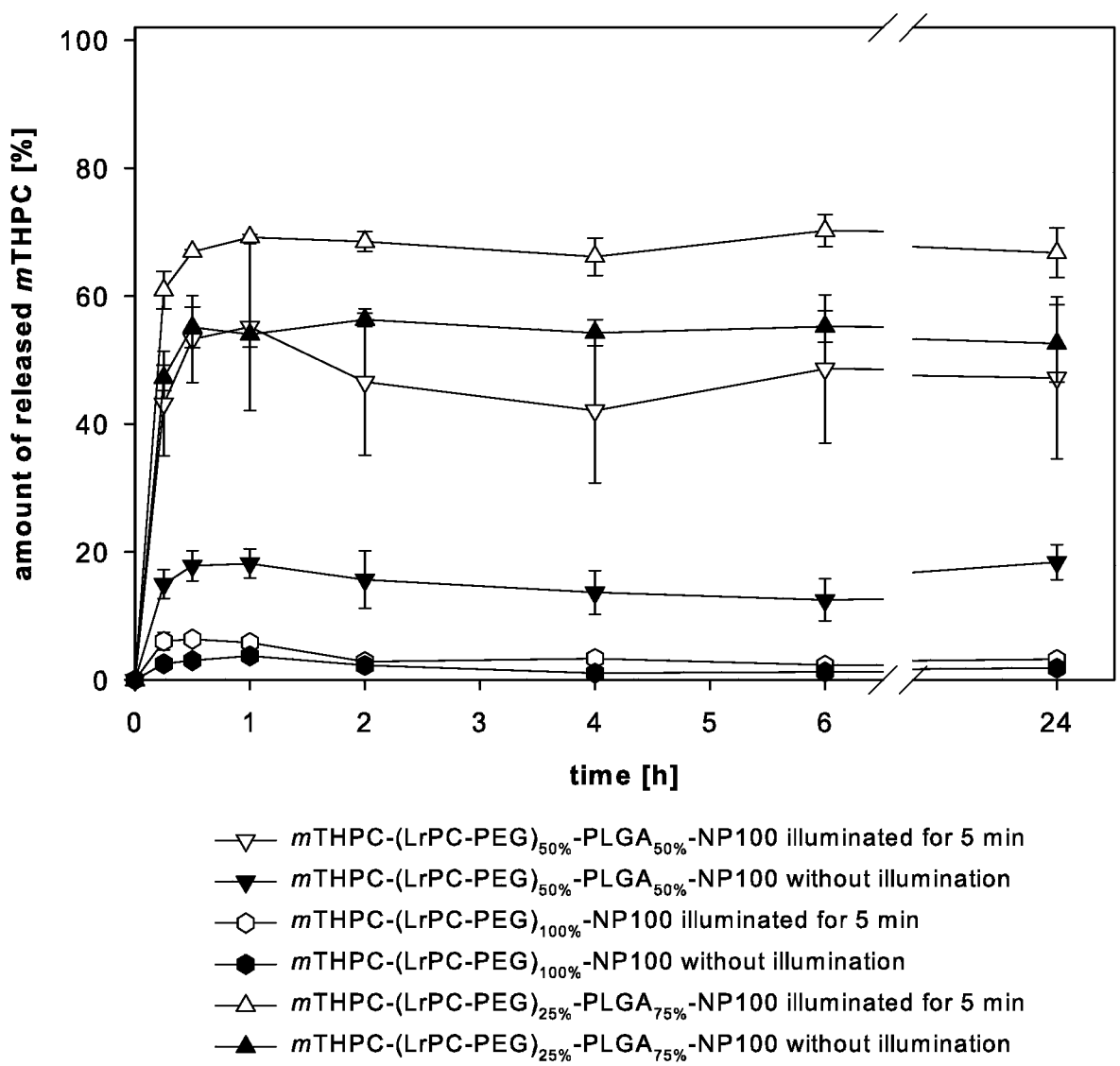
FIG. 7 shows the amount of the released PS mTHPC in dependence of particle light irradiation of mTHPC-(PC-PEG)$_{100\%}$-NP100 and mTHPC-(PC-PEG)$_{50\%}$-PLGA$_{50\%}$-NP100, and mTHPC-(PC-PEG)-PLGA-NP100 over 24 h.

The conducted in vitro release studies with (mTHPC-(PC-PEG)-PLGA-NP100) (FIGS. 5C and 7) showed that nanoparticles with 25% (PC-PEG) exhibited a high burst release, probably caused by the mixture of PLGA and (PC-PEG). To reduce the burst release, nanoparticles with 100% of (PC-PEG) were prepared. Unfortunately, the non-irradiated nanoparticles showed similar low mTHPC release as irradiated particles. Therefore, the light-triggered drug release of mTHPC-(PC-PEG)$_{100\%}$-NP100 did not lead to the desired results (FIG. 7).

In contrast, nanoparticles including 50% light-cleavable polymer (mTHPC-(PC-PEG)$_{50\%}$-PLGA$_{50\%}$-NP100) showed a small burst release when not irradiated and a significant increased drug release when irradiated. Hence, the increased amount of 50% (PC-PEG) in combination with 50% PLGA leads to a satisfying light-induced mTHPC-release characteristics (FIG. 7).

Example 3a

Biological Safety of Light-Cleavable Nanoparticles (NP) Based on Polycarbonate (PC) and Poly (DL-Lactide-Co-Glycolide) (PLGA) Before and After Irradiation with Light of a Wavelength of 365 nm Biological Safety Investigations of biological safety were performed using mucus producing HT-29-MTX cells. The used cells were cultivated in full supplemented DMEM. For investigations the following formulations were tested:

| 1. | PC-PLGA-NP100 | see Example 2a |
| 2. | PC-(PLA-PEG)-PLGA-NP100 | see Example 2b |
| 3. | (PC-PEG)-PLGA-NP100 | see Example 2c |

HT-29-MTX cells were incubated with a nanoparticle concentration ranging from 10 μg NP/mL to 500 μg NP/mL in DMEM (serum free), over a period of 24 h. After removal of the incubation medium, WST-1 reagent was added and absorbance was measured immediately at 460 nm with a Synergy MX multi-well spectrophotometer (BioTek Instruments GmbH, Bad Friedrichshall, Germany). Blank measurement, positive and negative control were used for calculation of total cell viability.

Figure 8:
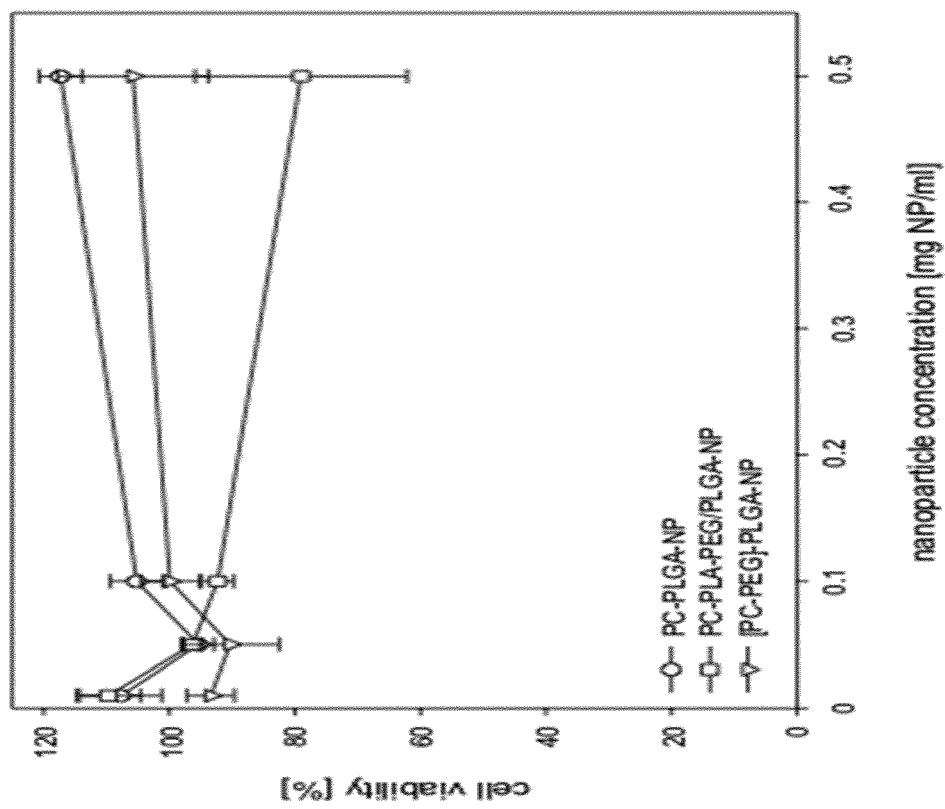
FIG. 8 shows the biological safety of unloaded light-cleavable nanoparticles before (A) and after (B) 5 min of irradiation with light of a wavelength of 365 nm measured by WST-1 cell viability assay.
Figure 8:
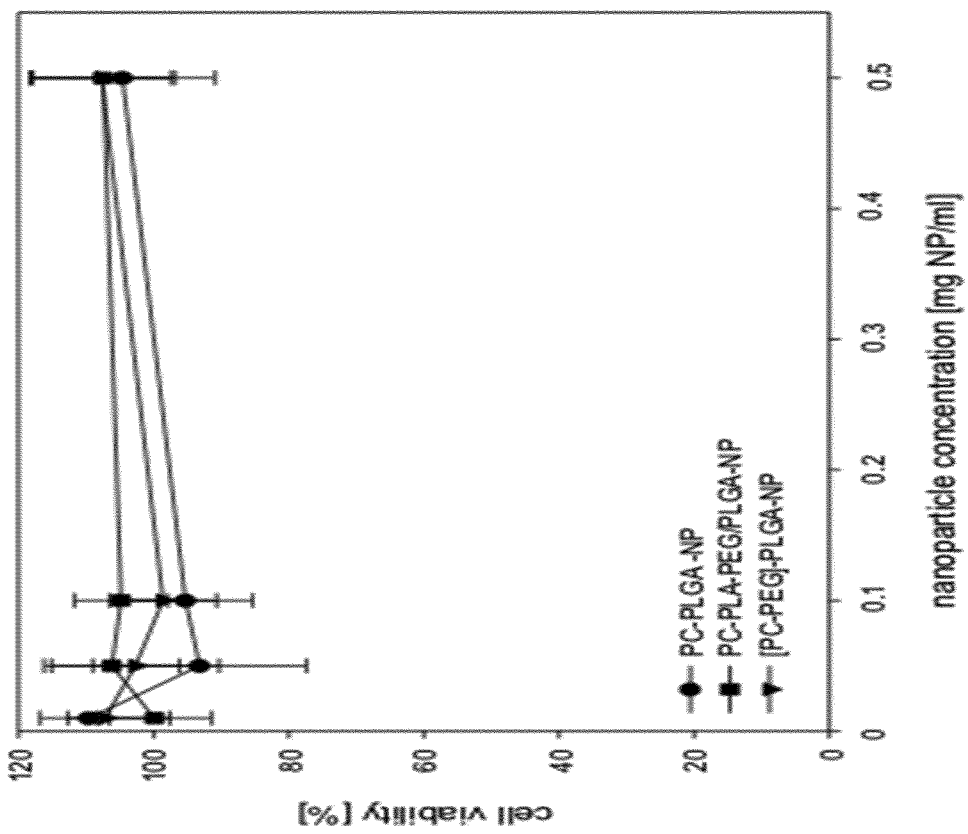

FIG. 8A illustrates the biological safety of all unloaded nanoparticles. The used cells show a viability of almost 100%, indicating no cytotoxicity for the used concentrations. The experiment was done in triplicate and for each experiment three measurements (n=3) were performed. Error bars represent the standard deviation of three experiments.

Biological Safety after Light Irradiation

For examination of cytotoxic effects after irradiation, the different formulations were irradiated for 5 min at 365 nm prior to cell incubation. Afterwards the HT-29-MTX cells were treated with the same concentration of irradiated formulations as described above.

FIG. 8B depicts biological safety for formulations after irradiation at 365 nm using HT-29-MTX cells. Cell viability shows no toxic effects of products after irradiation at 365 nm on the cells. The experiment was done in triplicate and for each experiment three measurements (n=3) were performed. Error bars represent the standard deviation of three experiments.

Example 3b

Analysis of Intracellular Uptake of Light-Cleavable Nanoparticles Based on Polycarbonate (PC) and Poly (DL-Lactide-Co-Glycolide) (PLGA) with the Photosensitizer (PS) 5,10,15,20-Tetrakis (3-Hydroxyphenyl)-Chlorin (mTHPC)

Intracellular Uptake Quantified by HPLC-FLD

Experiments to quantify the intracellular uptake in HT-29-MTX cells were performed for the following photosensitizer-loaded samples:

| 1. | mTHPC-PC-PLGA-NP100 | see Example 2a |
| 2. | mTHPC-PC-(PLA-PEG)-PLGA-NP100 | see Example 2b |

| | | |
|---|---|---|
| 3. | mTHPC-(PC-PEG)-PLGA-NP100 | see Example 2c |
| 4. | mTHPP-PLGA-NP100 | |
| 5. | mTHPC | |

The used cells, cultivated in DMEM, were incubated with nanoparticle concentrations corresponding to 1 µM mTHPC (mTHPP) for 24 h. At certain time points (1 h, 2 h, 4 h, 6 h and 24 h), incubation medium was removed, cells were washed (PBS, 2×) and cell amount and cell volume were determined using CASY® TT Cell Counter. After incubation, cells were transferred to DMSO for cell lysis and extraction of photosensitizer. Quantification of photosensitizer was performed by HPLC-FLD system (Agilent Technologies 1200 series). In samples dissolved in DMSO, cell debris was removed before HPLC analysis via centrifugation (30,000 g, 30 min). A reversed phase column (Gemini RP 18; 250×4.6 mm, particle diameter 5 µm (Phenomenex, Aschaffenburg, Germany) was used for isocratic elution with a mobile phase consisting of 57.7% acetonitrile and 42.5% water containing 0.1% (w/v) triflouroacetic acid (flow rate: 1.0 mL/min). The photosensitizer was detected at 421 nm excitation and 653 nm emission wavelength.

Figure 9:
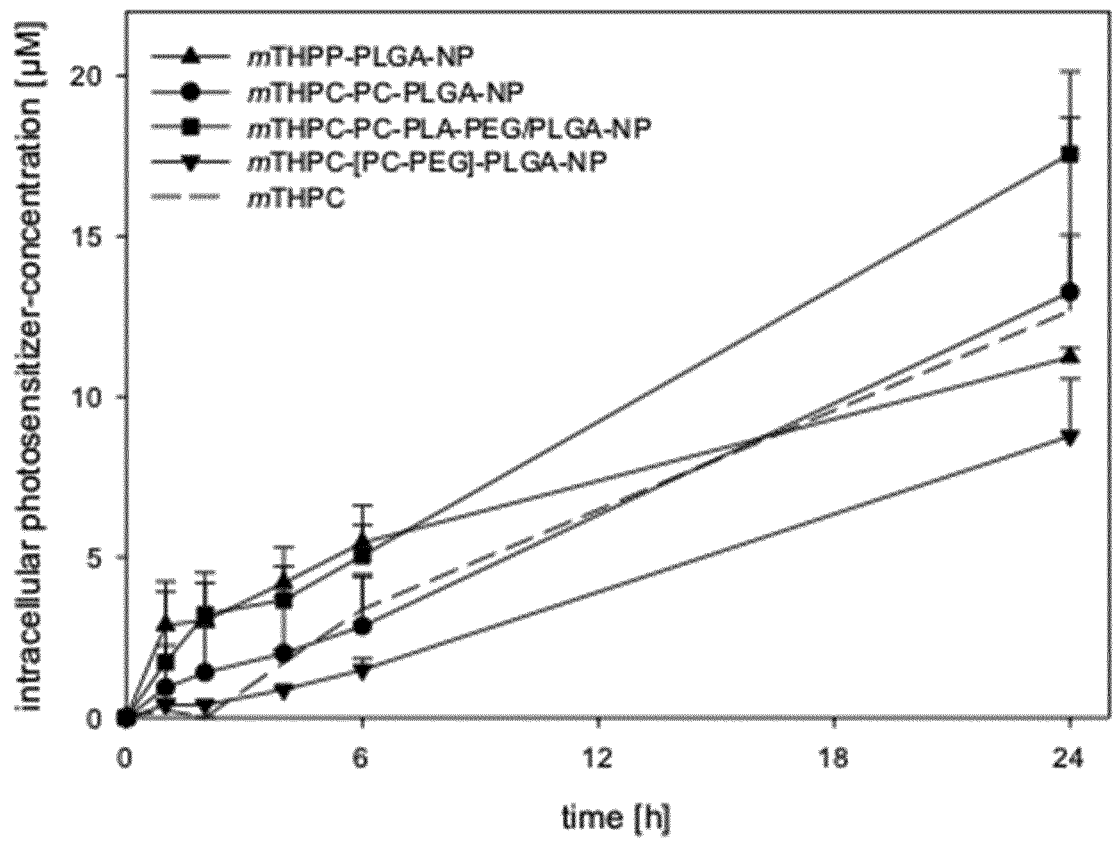
FIG. 9 depicts the intracellular uptake of mTHPC-loaded light-cleavable nanoparticles compared to free photosensitizer mTHPC and non-light cleavable mTHPP-PLGA-NP100 by HT-29-MTX cells over 24 h quantified via HPLC-FLD analysis.

FIG. 9 shows the results of the intracellular uptake of mTHPC and photosensitizer-loaded nanoparticles by HT-29-MTX cells over 24 h. Non-light-cleavable mTHPP-PLGA-NP100 and free mTHPC served as control. The experiment was done in triplicate and for each experiment three wells were incubated with the same concentration. Error bars represent the standard deviation of three experiments. The used nanoparticles were accumulated by a factor of 8 to 17 from the initial concentration. mTHPC-PC-PLGA-NP100 and mTHPC-PC-(PLA-PEG)-PLGA-NP100 were superior to non-light cleavable mTHPP-PLGA-NP100 and free mTHPC.

Cellular Association Quantified by IncuCyte® Live-Cell Imaging

Cellular association was investigated by IncuCyte® Live-Cell Imaging (Essen Bioscience, Inc., Michigan, USA) over a period of 24 h for the following samples:

| | | |
|---|---|---|
| 1. | mTHPC-PC-PLGA-NP100 | see Example 2a |
| 2. | mTHPC-PC-(PLA-PEG)-PLGA-NP100 | see Example 2b |
| 3. | mTHPP-PLGA-NP100 | |
| 4. | mTHPC | |

Cell incubations were performed using nanoparticle concentrations corresponding to 1 µM mTHPC (mTHPP).

Nine images were taken of each well and time point (every hour) over a period of 24 h. The red channel (excitation: 565-605 nm/emission: 625-705 nm) was used to quantify the total red object area representing the photosensitizer. Blank measurements were performed in wells containing cells but without nanoparticle incubation (medium).

Figure 10:
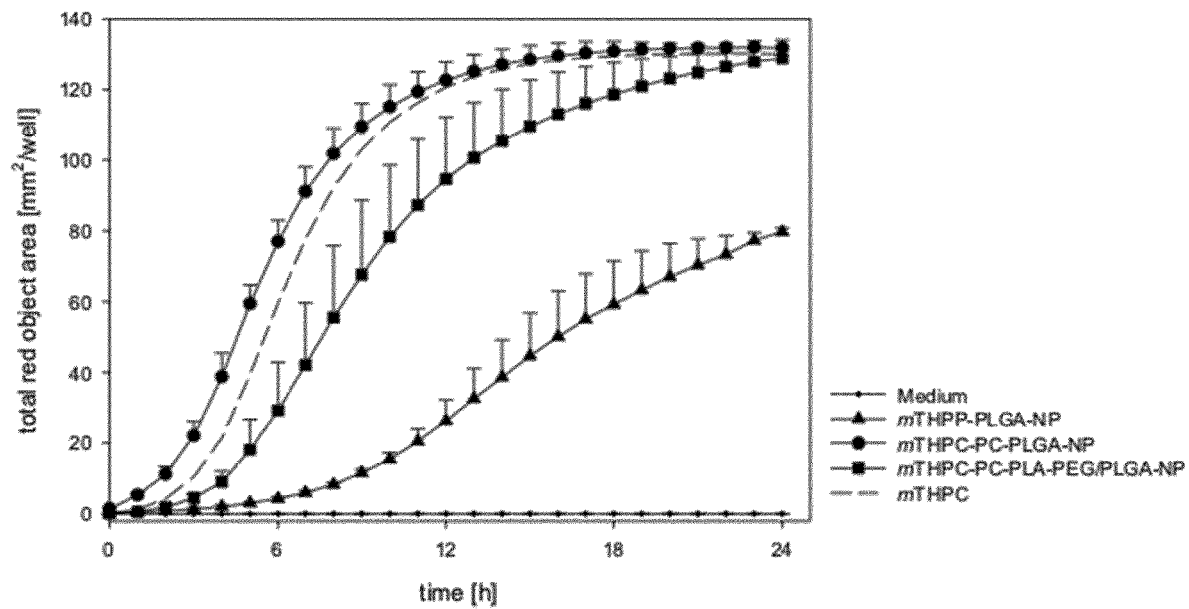
FIG. 10 shows the cellular association of mTHPC-loaded light-cleavable nanoparticles compared to mTHPC and non-light cleavable mTHPP-PLGA-NP100 by HT-29-MTX cells over 24 h quantified via red fluorescence of the photosensitizer using IncuCyte® Live-Cell Imaging.

FIG. 10 shows the results of the cellular association of mTHPC and photosensitizer-loaded nanoparticles by HT-29-MTX cells over 24 h. Non-light-cleavable mTHPP-PLGA-NP100 and free mTHPC served as control. The experiment was done in triplicate and for each experiment three wells were incubated with the same concentration. Error bars represent the standard deviation of three experiments. Light-cleavable nanoparticles showed the higher intensity of red fluorescence after 24 h compared to mTHPP-PLGA-NP.

Example 3c

Dark Toxicity and Photodynamic Activity of Light-Cleavable Nanoparticles Based on Polycarbonate (PC) and Poly (DL-Lactide-Co-Glycolide) (PLGA) with the Photosensitizer (PS) 5, 10, 15,20-Tetrakis (3-Hydroxyphenyl)-Chlorin (mTHPC)

Dark Toxicity

Investigation of dark toxicity of all mTHPC-loaded formulations was performed using WST-1 assay as described in Example 3a. HT-29-MTX cells were incubated with the following samples in a photosensitizer concentration ranging from 0.001 µM to 5 µM in DMEM over a period of 24 h:

| | | |
|---|---|---|
| 1. | mTHPC-PC-PLGA-NP100 | see Example 2a |
| 2. | mTHPC-PC-(PLA-PEG)-PLGA-NP100 | see Example 2b |
| 3. | mTHPC-(PC-PEG)-PLGA-NP100 | see Example 2c |
| 4. | mTHPP-PLGA-NP100 | |
| 5. | mTHPC | |

After removal of the incubation medium, WST-1 reagent was added and absorbance was measured immediately at 460 nm by a Synergy MX multi-well spectrophotometer. Blank measurement, positive and negative control were used for calculation of total cell viability.

Figure 11:
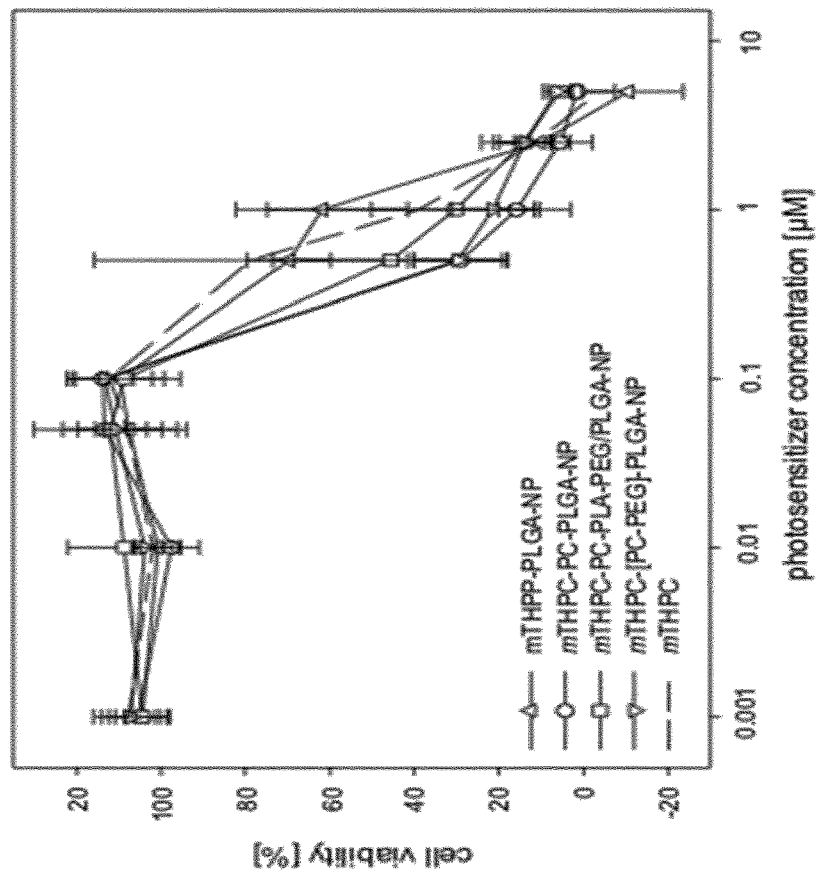
FIG. 11 depicts dark toxicity (A) and phototoxicity (B) of mTHPC-loaded light-cleavable nanoparticles. mTHPC and non-light-cleavable mTHPP-PLGA-NP100 served as control.
Figure 11:
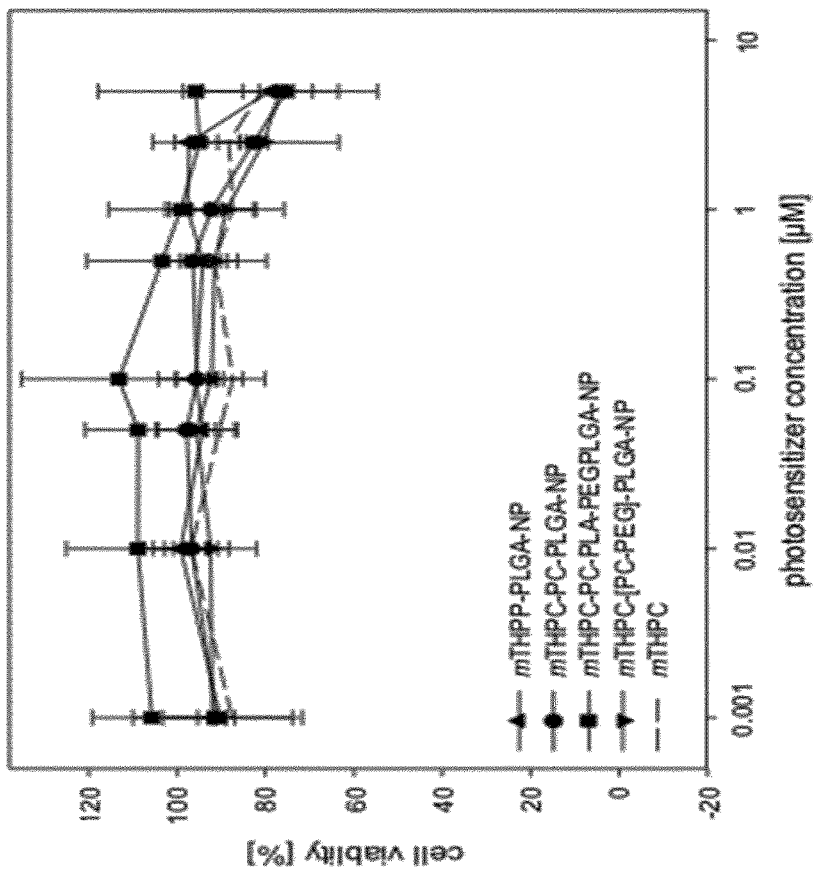

FIG. 11A shows the dark toxicity of all tested samples. With a viability of almost 100% no dark toxicity was detected in HT-29-MTX cells. Non-light-cleavable mTHPP-PLGA-NP100 and free mTHPC served as control. The experiment was done in triplicate and for each experiment three measurements (n=3) were performed. Error bars represent the standard deviation of three experiments.

Phototoxicity

For examination of photodynamic activity, after 24 h of incubation with tested formulations, cells were irradiated at 652 nm for 30 min at a light dose of 5 J/cm$^2$. Afterwards, WST-1 assay was performed as described above for evaluation of dark toxicity.

FIG. 11B demonstrates the phototoxicity effects on HT-29-MTX cells, indicating a comparable efficacy of the formulations of present invention to the pure photosensitizer mTHPC and the non-light cleavable control mTHPP-PLGA-NP100. The experiment was done in triplicate and for each experiment six measurements (n=6) were performed. Error bars represent the standard deviation of three experiments.

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

Example 3d

Photodynamic Activity after Nanoparticle Degradation of Light-Cleavable Nanoparticles Based on Polycarbonate (PC) and Poly (DL-Lactide-Co-Glycolide) (PLGA) with the Photosensitizer (PS) 5,10,15,20-Tetrakis (3-Hydroxyphenyl)-Chlorin (mTHPC)

A detailed investigation of toxicity after a two-wavelength irradition (365 nm for polymer/nanoparticle degradation; 652 nm for photosensitizer activation) was performed using WST-1 assay as described in Example 3a. HT-29-MTX cells were incubated with the following formulation in mTHPC concentrations ranging from 0.001 µM to 5 µM in DMEM over a period of 24 h.

| 1. | mTHPC-(PC-PEG)$_{50\%}$-PLGA$_{50\%}$-NP100 | see Example 2e |

For examination of photodynamic activity in combination with a light induced nanoparticle degradation, WST-1 assay was performed after three different ways of irradiation:
1. 365 nm (10 min)
2. 652 nm (30 min)
3. 365 nm (10 min) followed by 652 nm (30 min)

After irradiation, cells were stored in an incubator for 1 h. WST-1 reagent was added and absorbance was measured immediately at 460 nm by a Synergy MX multi-well spectrophotometer. Blank measurement, positive and negative control were used for calculation of total cell viability.

Figure 12:
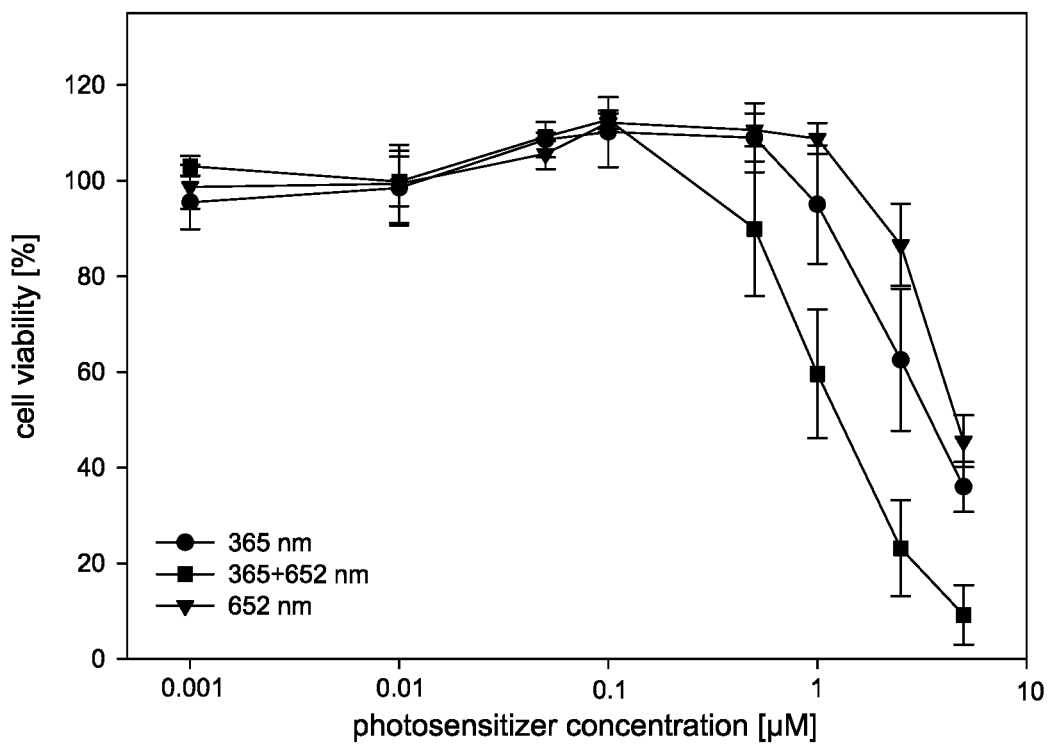
FIG. 12 shows the phototoxicity of mTHPC-(PC-PEG)$_{50\%}$-PLGA$_{50\%}$-NP100 after irradiation with light of a wavelength of 365 nm and 652 nm, separately and in combination.

FIG. 12 shows the toxicity of mTHPC-(PC-PEG)$_{50\%}$-PLGA$_{50\%}$-NP100 after irradiation at different wavelengths. The highest toxicity was observed after irradiation at both wavelengths, indicating a beneficial effect of nanoparticle degradation at 365 nm prior to activation of mTHPC at 652 nm. The irradiation with either 365 nm for nanoparticle degradation or 652 nm for photosensitizer activation led to a significantly reduced toxicity. The experiment was done in triplicate and for each experiment three measurements (n=3) were performed. Error bars represent the standard deviation of three experiments.

The work leading to this invention has received funding from BMBF under grant agreement n° BMBF 13N13423.

The invention claimed is:
1. A polymer, selected from the group consisting of a polycarbonate of formula 10

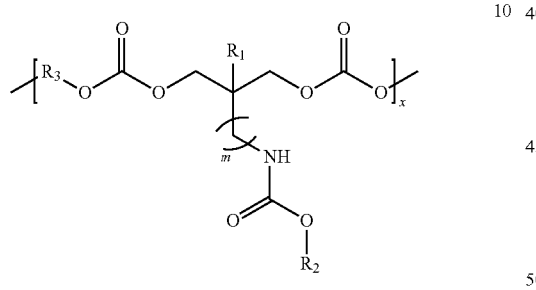

wherein n=0 or 1; x=+5-1000;
R$_1$ is H or an alkyl chain with 1 to 5 carbon atoms;
R$^2$ is selected from the group consisting of

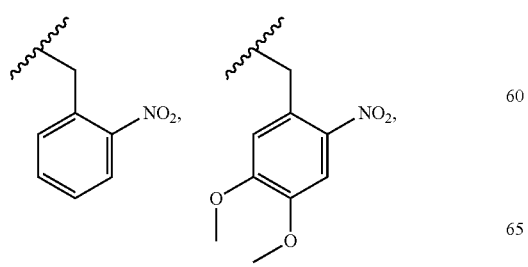

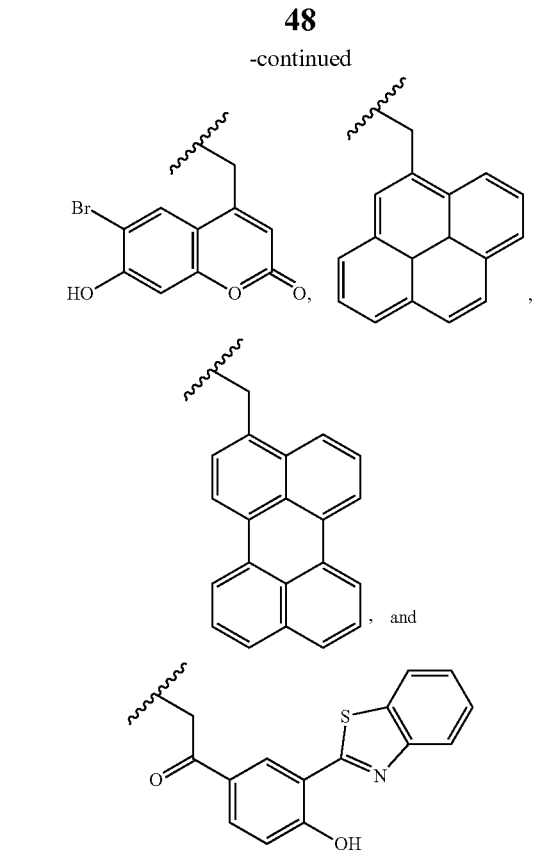

R$^3$ is a divalent radical selected from the group consisting of an alkyl, aryl and alkylene group having 1 to 10 carbon atoms;
a block copolymer of formula 12

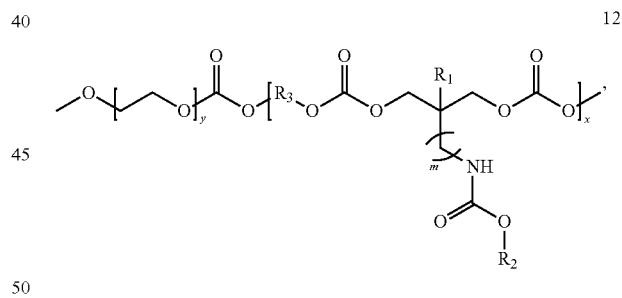

wherein n=0 or 1; x=45-1000; y=1-1000;
R$_1$ is H or an alkyl chain with 1 to 5 carbon atoms;
R$_2$ is selected from the groups consisting of

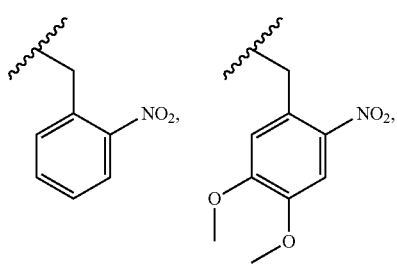

-continued

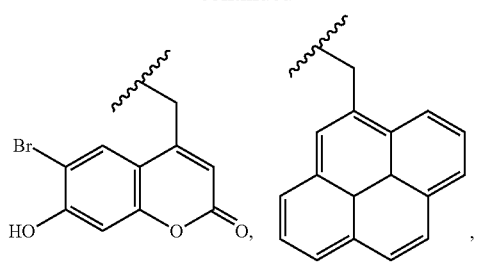

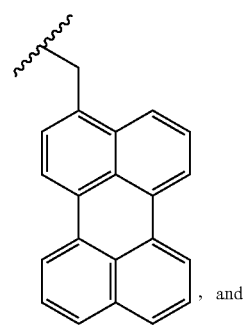, and

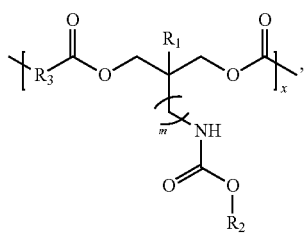

$R_3$ is a divalent radical selected from the group consisting of an alkyl, aryl and alkylene group having 1 to 10 carbon atoms; and a polyester of formula 13

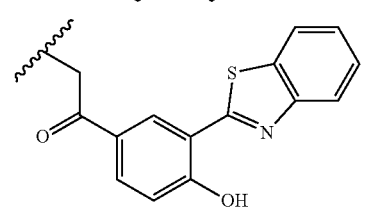   13 wherein n=0 or 1; x=5–1000;

$R_1$ is H or an alkyl chain with 1 to 5 carbon atoms;

$R_2$ is selected from the group consisting of

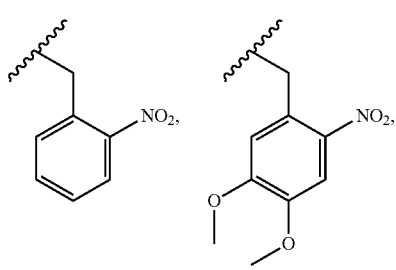

-continued

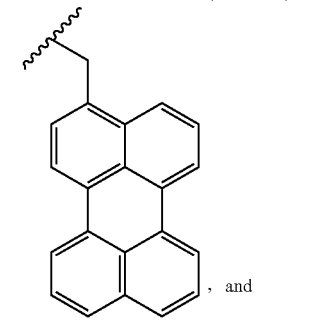

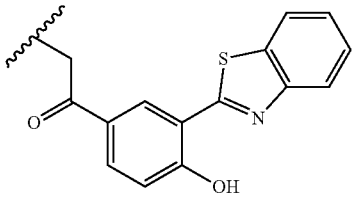, and

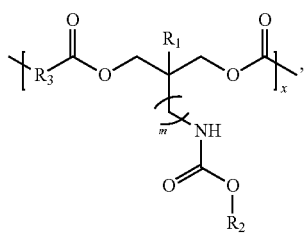

$R_3$ is selected from the group consisting of an alkyl, aryl and alkylene group having 1 to 10 carbon atoms.

2. A pharmaceutical composition, comprising
a light-cleavable polymer formed as nanometer particles, wherein the light-cleavable polymer comprises a polymer according to claim 1;
a therapeutically effective amount of a photosensitizer.

3. A pharmaceutical composition according to claim 2, characterized in that the photosensitizer is a tetrapyrrole-based photosensitizer.

4. A pharmaceutical composition according to claim 3, characterized in that the photosensitizer is a chlorin or bacteriochlorin derivative according to formula A

A

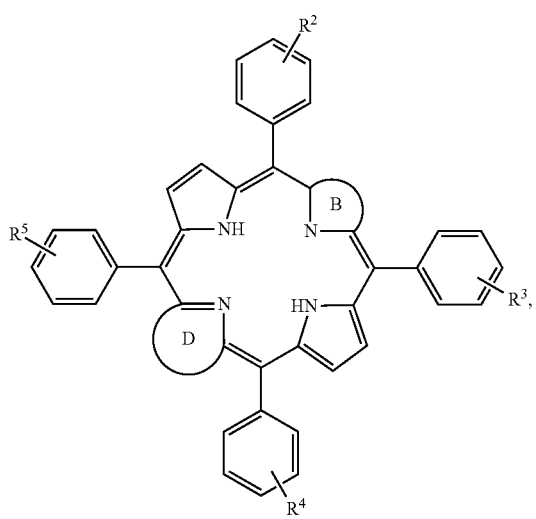

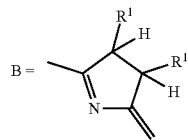

wherein:
$R_1$ is H or OH;
$R^2$ to $R^5$ are different or the same and comprise substituents either in the meta- or para-position of the phenyl ring with $R^2$ to $R^5$ independently of one another selected Y is a peptide or an oligopeptide wherein the n in formulas 10, 12 and 13=1-30;
from the group consisting of —OH, —COOH, —NH$_2$, —COOX, —NHX, OX, —NH—Y—COOH, and —CO—Y—NH$_2$;
wherein
X is (CH$_2$CH$_2$O)$_n$, CH$_3$ with the n in (CH$_2$CH$_2$O)$_n$CH$_3$=1–30 or a carbohydrate moiety;
Y is a peptide or an oligopeptide wherein the x in formulas 10, 12 and 13=5–30;
ring D has a structure selected from

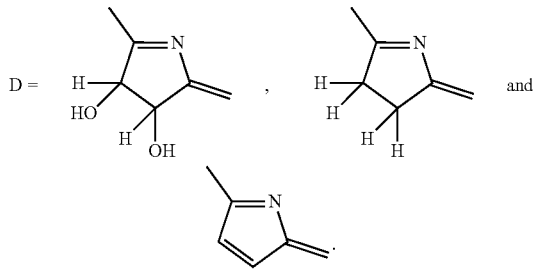

5. A pharmaceutical composition according to claim 2, characterized in that the photosensitizer is present in an amount of 1 to 500 μg per mg light cleavable polymer.

6. A pharmaceutical composition according to claim 2, characterized in that the photosensitizer is a tetrapyrrolic compound of formulas 14, 15, 16, 17, 18 or 19

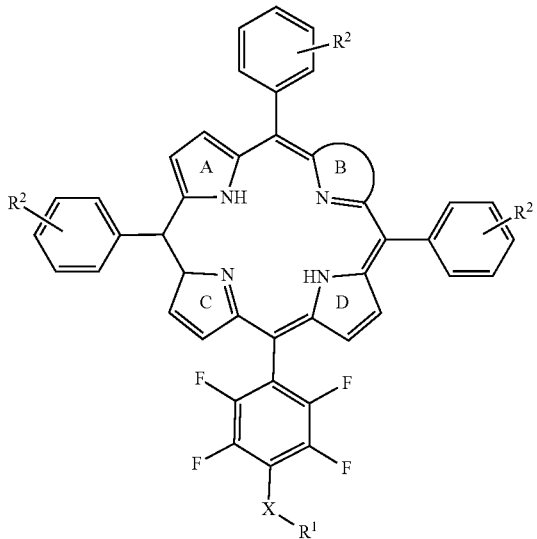

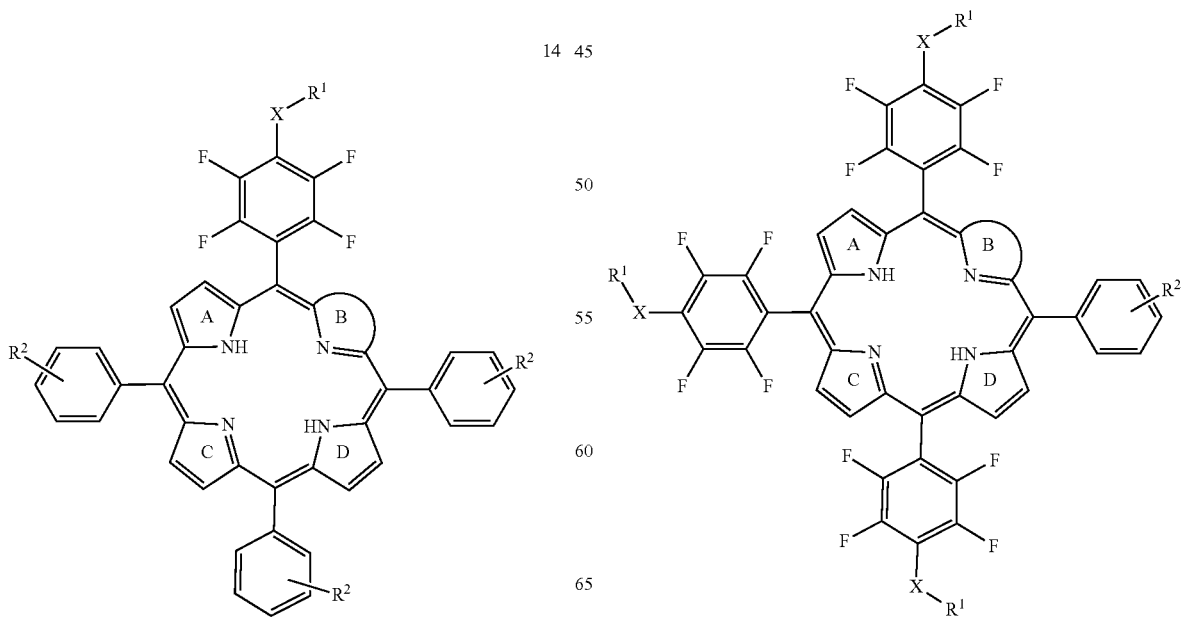

17

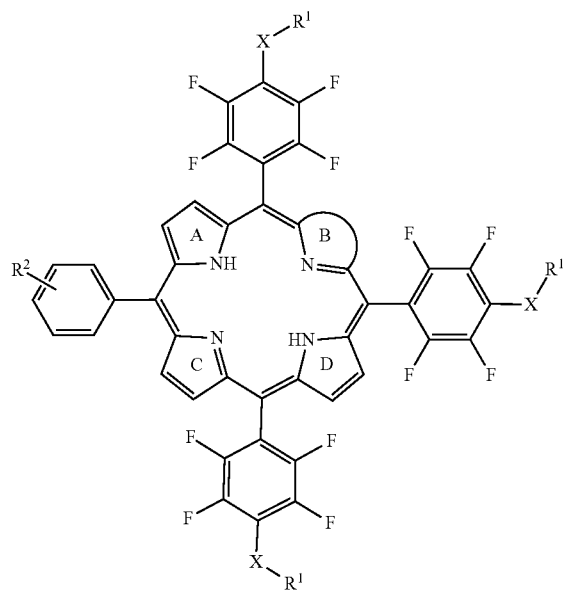

18

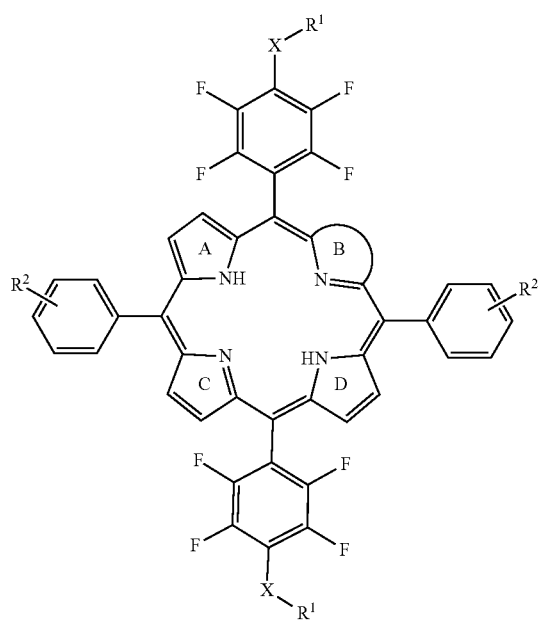

19

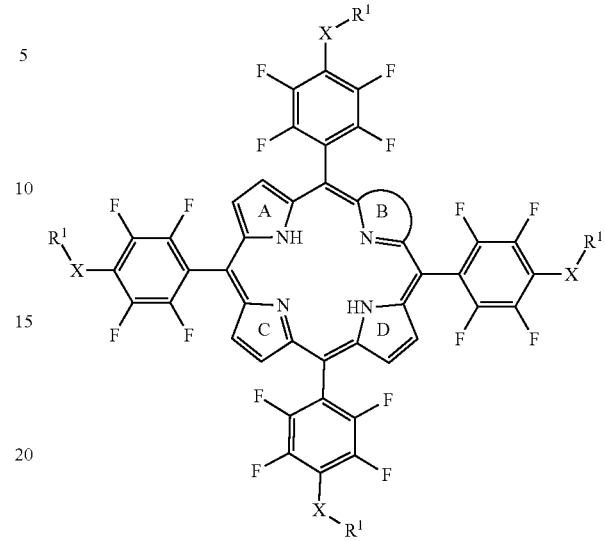

wherein
B is selected from

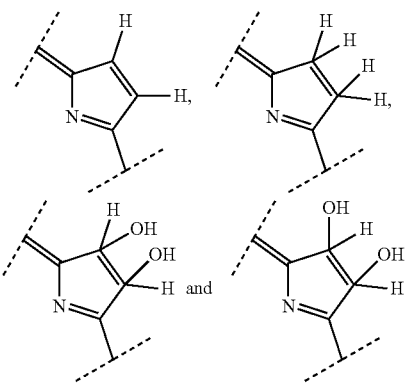

X is NH, O or S;
R$^1$ is a linear or branched alkyl chain with 3-4 carbon atoms and containing at least two hydroxyl moieties;
R$^2$ is a substituent either in the meta- or para-position of the phenyl ring wherein
R$^2$ is —OH, —COOH, —COOY, —NHY, OY, —NH—Z—COOH, or —CO—Z—NH$_2$;
wherein
Y is (CH$_2$CH$_2$O)$_n$CH$_3$ with the n in (CH$_2$CH$_2$O)$_n$CH$_3$=1-30 or a carbohydrate moiety; and
Z is selected from a peptide or an oligopeptide wherein the x in formulas 10, 12 and 13=5-30.

7. A method of forming a pharmaceutical composition according to claim 2, comprising the steps of:
a) dissolving the light-cleavable polymer alone or in combination with a further polymer in an organic solvent to form a polymer solution;
b) optionally dissolving a stabilizer in an aqueous solution to form a stabilizing solution;
c) optionally filtering said polymer solution and optionally said stabilizing solution through a filtration unit;
d) mixing the optionally filtered polymer solution with an aqueous solution;

e) evaporating the organic solvent;
f) purifying the formed nanoparticles; and
g) adding photosensitizer to the solution formed in step a) or to the purified nanoparticles formed in step f).

8. The method according to claim 7, characterized in that the stabilizing solution includes polyvinylalcohol.

9. The method according to claim 7, characterized in that the composition formed in step g) is freeze dried in the presence of cryoprotective agents.

10. The method according to claim 9, characterized in that the cryoprotective agents are selected from the group consisting of glucose, trehalose, sucrose, sorbitol, mannitol and combinations hereof.

11. The method according to claim 7, characterized in that the organic solvent used in step a) is a water-miscible compound.

12. The method according to claim 11, wherein the water miscible compound is acetone.

13. The method according to claim 7, characterized in that the organic solvent used in step
   a) is a water immiscible solvent.

14. The method according to claim 13, wherein the water immiscible solvent is dichloromethane.

15. A method of treating a patient with photodynamic therapy comprising administering light and a photsensitizer to the patient, wherein the photosensitizer comprises the pharmaceutical formulation of claim 2.

16. The method of claim 15, wherein the photodynamic therapy treats a condition selected from the group consisting of tumors, other neoplastic diseases, dermatological disorders, opthalmological disorders, urological disorders and arthritis.

* * * * *